(12) United States Patent
Schottek et al.

(10) Patent No.: US 7,105,690 B2
(45) Date of Patent: Sep. 12, 2006

(54) METHOD FOR PRODUCING TRANSITION METAL COMPOUNDS AND THEIR USE FOR THE POLYMERIZATION OF OLEFINS

(75) Inventors: Jörg Schottek, Frankfurt (DE); Gerhard Erker, Münster (DE); Klaus Kunz, Münster (DE); Steve Döring, Münster (DE)

(73) Assignee: Basell Polyolefine GmbH, Frankfurt (DE)

( * ) Notice: Subject to any disclaimer, the term of this patent is extended or adjusted under 35 U.S.C. 154(b) by 138 days.

(21) Appl. No.: 10/297,054

(22) PCT Filed: May 30, 2001

(86) PCT No.: PCT/EP01/06128

§ 371 (c)(1),
(2), (4) Date: Dec. 2, 2002

(87) PCT Pub. No.: WO01/92269

PCT Pub. Date: Dec. 6, 2001

(65) Prior Publication Data

US 2003/0191334 A1 Oct. 9, 2003

(51) Int. Cl.
*C07F 9/28* (2006.01)
*C07F 7/00* (2006.01)
*B01J 31/00* (2006.01)
*C08F 4/44* (2006.01)

(52) U.S. Cl. ............... 556/20; 556/52; 526/106; 526/943; 502/103; 502/117

(58) Field of Classification Search ............... 556/20, 556/52; 502/103, 117; 526/160, 943
See application file for complete search history.

(56) References Cited

U.S. PATENT DOCUMENTS

| | | | | |
|---|---|---|---|---|
| 5,026,798 A | 6/1991 | Canich | ..... | 526/127 |
| 5,350,723 A * | 9/1994 | Neithamer et al. | ..... | 502/104 |
| 5,416,178 A | 5/1995 | Winter | ..... | 526/160 |
| 5,661,096 A | 8/1997 | Winter | ..... | 502/103 |
| 5,679,811 A | 10/1997 | Winter | ..... | 556/7 |
| 5,703,257 A * | 12/1997 | Rosen et al. | ..... | 556/7 |
| 6,017,841 A | 1/2000 | Winter | ..... | 502/103 |
| 6,124,231 A | 9/2000 | Fritze et al. | ..... | 502/152 |
| 6,160,066 A * | 12/2000 | Canich | ..... | 526/160 |
| 6,172,168 B1 | 1/2001 | Winter | ..... | 526/127 |
| 6,255,531 B1 | 7/2001 | Fritz et al. | ..... | 568/3 |
| 6,271,164 B1 | 8/2001 | Fritze et al. | ..... | 502/104 |
| 6,329,313 B1 | 12/2001 | Fritze et al. | ..... | 502/202 |
| 6,350,829 B1 | 2/2002 | Lynch et al. | ..... | 526/151 |
| 6,583,237 B1 * | 6/2003 | Imuta et al. | ..... | 526/89 |

FOREIGN PATENT DOCUMENTS

| | | |
|---|---|---|
| DE | 196 06167 | 8/1997 |
| DE | 196 22207 | 12/1997 |
| EP | 302 424 | 2/1989 |
| EP | 601 830 | 6/1994 |
| EP | 811 627 | 12/1997 |
| EP | 824 112 | 2/1998 |
| EP | 824 113 | 2/1998 |
| EP | 924 223 | 6/1999 |
| WO | 94/28034 | 12/1994 |
| WO | 97/11775 | 4/1997 |
| WO | 99/40129 | 8/1999 |

OTHER PUBLICATIONS

Organometallics 2000, 19, 2556-2563, Steffen et al.
J. Am. Chem. Soc. 1995, 117, 6465-6474, Harlan et al.
Organometallics 1994, 2957-2969, Harlan et al.
Polyhedron, vol. 9, No. 2/3, 429-453, 1990, Pasynkiewicz.
JP 08198910-A, Abstract.

* cited by examiner

*Primary Examiner*—Porfirio Nazario-Gonzalez
(74) *Attorney, Agent, or Firm*—Novak, Druce, Quigg & DeLuca, LLP

(57) ABSTRACT

The invention relates to a method for producing special transition metal compounds, to novel transition metal compounds and to their use for the polymerization of olefins.

20 Claims, No Drawings

METHOD FOR PRODUCING TRANSITION METAL COMPOUNDS AND THEIR USE FOR THE POLYMERIZATION OF OLEFINS

The present invention relates to a process for preparing specific transition metal compounds, to novel transition metal compounds and to their use for the polymerization of olefins.

Metallocenes can, if appropriate in combination with one or more cocatalysts, be used as catalyst components for the polymerization and copolymerization of olefins. In particular, halogen-containing metallocenes are used as catalyst precursors which can be converted into a polymerization-active cationic metallocene complex, for example by means of an aluminoxane.

The preparation and use of monocyclopentadienyl compounds is known per se and is described, for example, in EP-A-0416815 and U.S. Pat. No. 5,026,798. For this purpose, it is possible, for example, to react cyclopentadienyl-metal compounds with halides or amides of transition metals such as titanium, zirconium and hafnium.

These "constrained geometry" catalysts described there display good polymerization properties in the copolymerization of ethylene and the higher olefins.

Changes in the activity and the copolymerization performance can be achieved by means of changes in the bridging atoms between cyclopentadienyl ligands and the coordination site on the metal atom. A few different bridges are known for this purpose and are described, for example, in Organometallics 2000, 19, 2556–2563. However, these compounds do not have the classical constrained geometry and are therefore not suitable for industrial use.

In addition, the preparation of the complexes is carried out via a multistage synthesis and sometimes gives poor yields, which leads directly to increased costs and thus to only limited commercial utility.

It is an object of the present invention to find a new synthetic route to this class of compounds which avoids the disadvantages of the above-described prior art.

We have found that this object is achieved by using substituted or unsubstituted fulvenes, aminofulvenes or systems having a structure analogous to that of fulvene to provide a universal route to the above-described class of compounds.

The present invention accordingly provides a process for preparing compounds of the formula (VII)

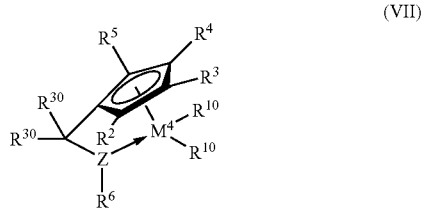

(VII)

where
$R^{30}$ is a hydrogen atom, $C_1$–$C_{18}$-alkyl such as methyl, ethyl, n-butyl, n-hexyl, tert-butyl, isopropyl, isobutyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl such as phenyl, tolyl, xylyl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably hydrogen, $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably hydrogen, methyl, ethyl, n-butyl, n-hexyl, tert-butyl, phenyl or tolyl, where the $R^{30}$ ligands may be identical or different,
$R^2$, $R^3$, $R^4$, $R^5$ are identical or different and are each a hydrogen atom, $C_1$–$C_{18}$-alkyl such as methyl, ethyl, n-butyl, n-hexyl, isopropyl, isobutyl, $C_3$–$C_{12}$ cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, isopropyl, isobutyl $C_6$–$C_{18}$-aryl such as phenyl, tolyl, xylyl, particularly preferably methyl, ethyl, n-butyl, n-hexyl, tert-butyl, phenyl or tolyl, where the radicals $R^2$, $R^3$, $R^4$ and $R^5$ may together form cyclic systems such as indenyls, benzindenyls, fluorenyl and phenanthryl which may in turn be substituted,
$R^6$ is a hydrogen atom or a $C_1$–$C_{20}$ group, preferably $C_1$–$C_{18}$-alkyl such as methyl, ethyl, n-butyl, n-hexyl, tert-butyl, isobutyl, isopropyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl such as phenyl, tolyl, xylyl, $C_5$–$C_{18}$-heteroaryl such as furanyl, pyridinyl, $C_7$–$C_{20}$-arylalkyl, $C_7$–$C_{20}$-alkylaryl, preferably hydrogen, $C_1$–$C_{18}$-alkyl such as methyl, ethyl, cyclohexyl, $C_6$–$C_{18}$-aryl such as phenyl, tolyl,
$R^{10}$ is a hydrogen atom, a halogen atom, a $C_1$–$C_{20}$ group such as methyl, ethyl, propyl, isopropyl, isobutyl, $C_5$–$C_{20}$-aryl such as phenyl, tolyl, xylyl, $C_5$–$C_{20}$-aryloxy such as substituted or unsubstituted phenoxy and biphenoxy, $C_1$–$C_{20}$-alkyloxy, a nitrogen-containing compound, preferably fluorine or chlorine, methyl, ethyl, phenyl, substituted or unsubstituted phenoxy, $NMe_2$, $NEt_2$, very particularly preferably chlorine, $NMe_2$, $NEt_2$,
Z is phosphorus, oxygen, nitrogen or sulfur, particularly preferably phosphorus or nitrogen,
$M^4$ is an element of groups 3 to 10 of the Periodic Table of the Elements, preferably titanium, zirconium, hafnium, vanadium, niobium, tantalum, chromium, molybdenum or tungsten, very particularly preferably titanium, zirconium or hafnium, comprising the steps
A) reacting a compound of the formula I

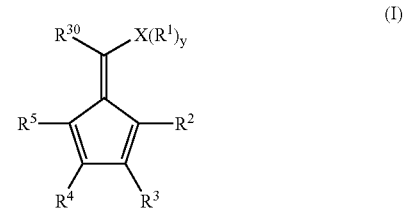

(I)

where
$R^1$ is a hydrogen atom, $C_1$–$C_{18}$-alkyl such as methyl, ethyl, n-butyl, n-hexyl, tert-butyl, isopropyl, isobutyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl, such as phenyl, tolyl, xylyl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably methyl, ethyl, n-butyl, n-hexyl, tert-butyl, phenyl or tolyl and $R^2$, $R^3$, $R^4$, $R^5$ are as defined under formula (VII), X is oxygen, nitrogen or sulfur, particularly preferably nitrogen, y is 1 or 2, with a compound of the formula (II),

$$M^1R^6ZR^7 \qquad (II)$$

where

Z and $R^6$ are as defined under formula (VII), $M^1$ is an element of group 1 or 2 of the Periodic Table of the Elements, preferably lithium, sodium, potassium or magnesium, particularly preferably lithium, $R^7$ is a hydrogen atom, $C_1-C_{18}$-alkyl such as methyl, ethyl, n-butyl, n-hexyl, tert-butyl, isopropyl, isobutyl, $C_3-C_{12}$-cycloalkyl, cyclopentyl, cyclohexyl or cyclooctyl, $C_2-C_{10}$-alkenyl, $C_3-C_{15}$-alkylalkenyl, $C_6-C_{18}$-aryl such as phenyl, tolyl, xylyl, $C_5-C_{18}$-heteroaryl such as furanyl, pyridinyl, $C_7-C_{20}$-arylalkyl, $C_7-C_{20}$-alkylaryl, fluorinated $C_1-C_{12}$-alkyl, fluorinated $C_6-C_{18}$-aryl, fluorinated $C_7-C_{20}$-arylalkyl or fluorinated $C_7-C_{20}$-alkylaryl, preferably hydrogen, $C_1-C_{18}$-alkyl such as methyl, ethyl, n-butyl, n-hexyl, tert-butyl, isopropyl, isobutyl, $C_6-C_{18}$-aryl such as phenyl, tolyl, xylyl, particularly preferably hydrogen, methyl, ethyl, n-butyl, n-hexyl, tert-butyl, phenyl or tolyl, to form a compound of the formula (III)

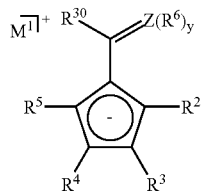

(III)

Where $R^2$, $R^3$, $R^4$, $R^5$, $R^6$, $R^{30}$, Z, $M^1$ and y are as defined above, B) reacting the compound of the formula (III) obtained in step A) with a compound of the formula IV $$M^2R^8 \qquad (IV)$$

where $M^2$ is an element of group 1 or 2 of the Periodic Table of the Elements, preferably lithium, sodium, potassium or magnesium, particularly preferably lithium, $R^8$ is preferably a hydrogen atom or $C_1-C_{18}$-alkyl such as methyl, ethyl, n-butyl, n-hexyl, tert-butyl, sec-butyl, particularly preferably methyl, n-butyl, sec-butyl, to form a compound of the formula (V)

(V)

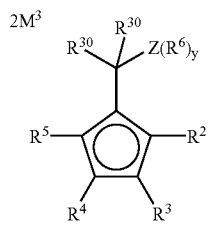

where $R^2$, $R^3$, $R^4$, $R^5$, $R^6$, $R^{30}$, Z and y are as defined above and $M^3$ is an element of group 1 or 2 of the Periodic Table of the Elements, preferably lithium, sodium, potassium or magnesium, particularly preferably lithium, and is identical to $M^1$ or $M^2$, and C) reacting the compound of the formula (V) obtained in step (B) with a compound of the formula (VI)

$$M^4(R^9)_f(R^{10})_g(R^{11})_k \qquad (VI)$$

where $M^4$ is an element of groups 3 to 8 of the Periodic Table of the Elements, particularly preferably titanium, zirconium, hafnium, vanadium, niobium, tantalum, chromium, molybdenum or tungsten, very particularly preferably titanium, zirconium or hafnium, $R^9$ is a hydrogen atom, a halogen atom, a $C_1-C_{20}$ group such as methyl, ethyl, propyl, isopropyl, a $C_5-C_{20}$ aryl such as phenyl, tolyl, xylyl, $C_5-C_{20}$-aryloxy such as substituted or unsubstituted phenoxy or biphenoxy, preferably fluorine or chlorine, methyl, ethyl, phenyl, substituted or unsubstituted phenoxy, very particularly preferably chlorine, methyl, phenyl, $R^{10}$ is a hydrogen atom, a halogen atom, a $C_1-C_{20}$ group such as methyl, ethyl, propyl, isopropyl, isobutyl, $C_5-C_{20}$-aryl such as phenyl, tolyl, xylyl, $C_5-C_{20}$-aryloxy such as substituted or unsubstituted phenoxy or biphenoxy, a nitrogen-containing radical, preferably fluorine or chlorine, methyl, ethyl, phenyl, substituted or unsubstituted phenoxy, $NMe_2$, $NEt_2$, very particularly preferably chlorine, $NMe_2$, $NEt_2$, $R^{11}$ is a $C_1-C_{20}$-heteroorganic compound, preferably linear or cyclic or aromatic ethers or thioethers, e.g. diethyl ether, methyl tert-butyl ether, dimethoxyethane, diisopropyl ether, di-n-butyl ether, tetrahydrofuran, tetrahydrothiophene, very particularly preferably diethyl ether or tetrahydrofuran, f is 1–10, preferably 1–6, very preferably 2, g is 1–10, preferably 1–6, very preferably 2, k is 1–10, preferably 1–6, very preferably 2, to give the compound of the formula (VII).

A compound of the formula (I) can firstly be placed in a reaction vessel. The compound can either be dissolved or suspended in a solvent or can also be present as such. Suitable solvents are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert butyl ether, dimethoxyethane, diisopropyl ether, di-n-butyl ether, anisole or mixtures of these. The compound is initially charged at from −100° C. to 300° C., preferably from −80° C. to 200° C., particularly preferably from 20° C. to 150° C. The compound of the formula (I) is advantageously present in a liquid phase.

A compound of the formula (II) can subsequently be added. This can likewise be dissolved or suspended in a solvent or can be added as such. Suitable solvents are those described above; preference is given to using the same solvent. The addition can be carried out over a period of from 1 minute to 96 hours, preferably from 10 minutes to 8 hours. The temperature of the initial charge during the addition is generally from −100° C. to 200° C., preferably from −80° C. to 150° C., particularly preferably from 20° C. to 150° C. The temperature is generally selected so that at least one reactant is present in a liquid phase. The subsequent reaction temperature is generally in a preferred range from 20° C. to 150° C. Furthermore, the reaction can be carried out at atmospheric pressure but can also be carried out at superatmospheric pressure, although this requires appropriate reactors. The molar ratio in which the compounds of the formula (I) and (II) are combined, based on the amount of $M^1$ in the compounds of the formula (II) used, is from 1:1000 to 1:0.01. Preference is given to a ratio of compounds of the formula (I) to amount of $M^1$ in the compound of the formula (I) of from 1:100 to 1:0.1. Particular preference is given to a stoichiometric reaction based on the compounds of the formulae (I) and (II).

The compounds of the formula II can be used as pure substances or can be generated in situ from a base such as lithium diisopropylamide and an amine. Nonlimiting examples of preferred compounds of the formula (II) are: lithium phosphide, lithium cyclohexylphosphide, lithium cyclopentylphosphide, lithium phenylphosphide, lithium methylphosphide, lithium tert-butylphosphide, lithium 2,6-(diisopropyl)phenylphosphide, lithium ethylphosphide, lithium isopropylphosphide, lithium 2,6-(di-tert-butyl)phenylphosphide, lithium 2,6-(dimethyl)phenylphosphide, lithium 2,6-(diethyl)phenylphosphide, lithium 3-methylphenylphosphide, lithium 3-ethylphenylphosphide, lithium 2,5-(diisopropyl)phenylphosphide, lithium 4-ethylphenylphosphide, lithium 4-isopropylphenylphosphide, lithium 2,5-(di-tert-butyl)phenylphosphide, lithium 2,5-(dimethyl) phenylphosphide, lithium 2,5-(diethyl)phenylphosphide, lithium 2,3-(diisopropyl)phenylphosphide, lithium 2,3-(di-tert-butyl)phenylphosphide, lithium 2,3-(dimethyl)phenylphosphide, lithium 2,3-(diethyl)phenylphosphide, lithium 2,4-(diisopropyl)phenylphosphide, lithium 2,4-(di-tert-butyl)phenylphosphide, lithium 2,4-(dimethyl)phenylphosphide, lithium 2,4-(diethyl)phenylphosphide, sodium phenylphosphide, sodium 4-methylphenylphosphide, sodium tert-butylphenylphosphide, sodium tert-butylphosphide, sodium 2,6-(diisopropyl)phenylphosphide, sodium 4-ethylphenylphosphide, sodium 4-isopropylphenylphosphide, sodium 2,6-(di-tert-butyl)phenylphosphide, sodium 2,6-(dimethyl)phenylphosphide, sodium 2,6-(diethyl)phenylphosphide, sodium 3-methylphenylphosphide, sodium 3-ethylphenylphosphide, sodium 2,5-(diisopropyl) phenylphosphide, sodium 4-ethylphenylphosphide, sodium 4-isopropylphenylphosphide, sodium 2,5-(di-tert-butyl)phenylphosphide, sodium 2,5-(dimethyl)phenylphosphide, sodium 2,5-(diethyl)phenylphosphide, sodium 2,3-(diisopropyl)phenylphosphide, sodium 4-ethylphenylphosphide, sodium 4-isopropylphenylphosphide, sodium 2,3-(di-tert-butyl)phenylphosphide, sodium 2,3-(dimethyl)phenylphosphide, sodium 2,4-(diisopropyl)phenylphosphide, sodium 4-ethylphenylphosphide, sodium isopropylphosphide, sodium 2,4-(di-tert-butyl)phenylphosphide, sodium 2,4-(dimethyl)phenylphosphide, sodium 2,4-(diethyl)phenylphosphide, potassium phenylphosphide, potassium methylphosphide, potassium tert-butylphenylphosphide, potassium tertbutylphosphide, potassium 2,6-(diisopropyl) phenylphosphide, potassium 4-ethylphenylphosphide, potassium 4-isopropylphenylphosphide, potassium 2,6-(di-tert-butyl)phenylphosphide, potassium 2,6-(dimethyl)phenylphosphide, potassium 2,6-(diethyl)phenylphosphide, potassium 3-methylphenylphosphide, potassium 3-ethylphenylphosphide, potassium 2,5-(diisopropyl)phenylphosphide, potassium 4-ethylphenylphosphide, potassium 4-isopropylphenylphosphide, potassium 2,5-(di-tert-butyl)phenylphosphide, potassium 2,5-(dimethyl) phenylphosphide, potassium 2,5-(diethyl)phenylphosphide, potassium 2,3-(diisopropyl)phosphide, potassium 4-ethylphenylphosphide, potassium 4-isopropylphenylphosphide, potassium 2,3-(di-tert-butyl)phenylphosphide, potassium 2,3-(dimethyl)phenylphosphide, potassium 2,3-(diethyl)phenylphosphide, potassium 2,4-(diisopropyl) phenylphosphide, potassium 4-ethylphenylphosphide, potassium 4-isopropylphenylphosphide, potassium 2,4-(di-tert-butyl)phenylphosphide, potassium 2,4-(dimethyl)phenylphosphide, potassium 2,4-(diethyl)phenylphosphide.

In the next step, one or more compounds of the formula (III) can be placed in a reaction vessel. The compounds can either be dissolved or suspended in a solvent or can also be present as such. Suitable solvents are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert butyl ether, dimethoxyethane, diisopropyl ether, di-n-butyl ether, anisole or mixtures of these. The compound is initially charged at generally from −100° C. to 300° C., preferably from −80° C. to 200° C., particularly preferably from 20° C. to 150° C. The compound of the formula (III) is advantageously present in a liquid phase.

One or more compounds of the formula (IV) can subsequently be added. These can likewise be dissolved or suspended in a solvent or can be added as such. Suitable solvents are those described above; preference is given to using the same solvent. The addition can be carried out over a period of from 1 minute to 96 hours, preferably from 10 minutes to 8 hours. The temperature of the initial charge during the addition is generally from −100° C. to 200° C., preferably from −80° C. to 150° C., particularly preferably from 20° C. to 150° C. The temperature is generally selected so that at least one reactant is present in a liquid phase. The subsequent reaction temperature is generally in a preferred range from 20° C. to 150° C. Furthermore, the reaction can be carried out at atmospheric pressure but can also be carried out at superatmospheric pressure, although this requires appropriate reactors. The molar ratio in which the compounds of the formula (III) and (IV) are combined, based on the amount of $M^2$ in the compounds of the formula (IV) used, is from 1:1000 to 1:0.01. Preference is given to a molar ratio of compounds of the formula (III) to the amount of $M^2$ in the compounds of the formula (IV) used of from 1:100 to 1:0.1. Particular preference is given to a stoichiometric reaction based on the compounds of the formula (III) and (IV).

The compound V can be isolated or prepared and reacted in situ.

In a variant of the process of the present invention, the compound of the formula V is prepared by reacting a compound of the formula VIII (in place of the compound of the formula I)

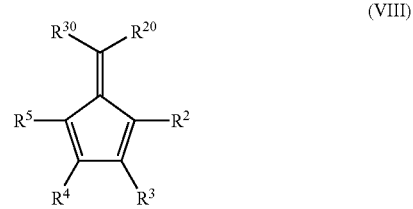

(VIII)

where
$R^{30}$ is as defined above,
$R^{20}$ is a hydrogen atom, $C_1$–$C_{18}$-alkyl such as methyl, ethyl, n-butyl, n-hexyl, tert-butyl, isopropyl, isobutyl, $C_3$–$C_{12}$- cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl, such as phenyl, tolyl, xylyl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably hydrogen, $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably hydrogen, methyl, ethyl, n-butyl, n-hexyl, tert-butyl, phenyl or tolyl and $R^2$, $R^3$, $R^4$, $R^5$ are as defined under formula (VII),
with a compound of the formula (II), $$M^1R^6ZR^7 \qquad (II)$$

where
Z, $R^6$, $M^1$ and $R^7$ are as defined above,
to form a compound of the formula (IX)

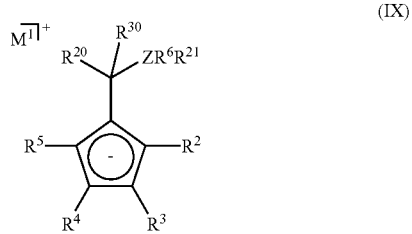

where $R^2$, $R^3$, $R^4$, $R^5$, $R^6$, $R^{20}$, $R^{30}$, Z, $M^1$ are as defined above and
$R^{21}$ is a hydrogen atom, $C_1$–$C_{18}$-alkyl such as methyl, ethyl, n-butyl, n-hexyl, tert-butyl, isopropyl, isobutyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl such as phenyl, tolyl, xylyl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably methyl, ethyl, n-butyl, n-hexyl, tert-butyl, phenyl or tolyl,
and subsequently reacting the compound of the formula IX with a compound of the formula X $$M^5R^{22} \qquad (X)$$

where
$M^2$ is an element of group 1 or 2 of the Periodic Table of the Elements, preferably lithium, sodium, potassium or magnesium, particularly preferably lithium,
$R^{22}$ is $C_1$–$C_{18}$-alkyl such as methyl, ethyl, n-butyl, n-hexyl, tert-butyl, sec-butyl, particularly preferably methyl, n-butyl, sec-butyl, or an $N(R^{50})_p$ unit in which $R^{50}$ is preferably $C_1$–$C_{18}$-alkyl such as methyl, ethyl, n-butyl, n-hexyl, tert-butyl, sec-butyl, isopropyl, particularly preferably methyl, ethyl, tert-butyl or isopropyl and p=2,
to give the above-described compound of the formula V.

The compounds of the formula X can be used as pure substances or can be generated in situ. Nonlimiting examples of preferred compounds of the formula (X) are:
lithium diisopropylamide, lithium dimethylamide, lithium diethylamide, lithium diphenylamide, lithium dicyclohexylamide, lithium dibenzylamide, lithium isopropylmethylamide, lithium dibutylamide, lithium di-tert-butylamide, lithium ditolylamide, lithium dicyclopentylamide, lithium dibutylamide, lithium methylethylamide, lithium ethylbutylamide, sodium diisopropylamide, sodium dimethylamide, sodium diethylamide, sodium diphenylamide, sodium dicyclohexylamide, sodium dibenzylamide, sodium isopropylmethylamide, sodium dibutylamide, sodium di-tert-butylamide, sodium ditolylamide, sodium dicyclopentylamide, sodium dibutylamide, sodium methylethylamide, sodium ethylbutylamide, potassium diisopropylamide, potassium dimethylamide, potassium diethylamide, potassium diphenylamide, potassium dicyclohexylamide, potassium dibenzylamide, potassium isopropylmethylamide, potassium dibutylamide, potassium di-tert-butylamide, potassium ditolylamide, potassium dicyclopentylamide, potassium dibutylamide, potassium methylethylamide and/or potassium methylbutylamide.

The reaction conditions and stoichiometric ratios for this variant of the process of the present invention for preparing compound V are analogous to those described above for the reactions of compounds of the formula I with compounds of the formula II and for the reactions of compounds of the formula III with the compound of the formula IV.

In the next step, one or more compounds of the formula (V) can be placed in a reaction vessel. The compounds can either be dissolved or suspended in a solvent or can also be present as such. Suitable solvents are generally aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and also ethers such as diethyl ether, methyl tert butyl ether, dimethoxyethane, diisopropyl ether, di-n-butyl ether, anisole or mixtures of these. The compound is initially charged at generally from −100° C. to 300° C., preferably from −80° C. to 200° C., particularly preferably from 20° C. to 150° C. The compound of the formula (V) is advantageously present in a liquid phase.

One or more compounds of the formula (VI) can subsequently be added. These can likewise be dissolved or suspended in a solvent or can be added as such. Suitable solvents are those described above; preference is given to using the same solvent. The addition can be carried out over a period of from 1 minute to 96 hours, preferably from 10 minutes to 8 hours. The temperature of the initial charge during the addition is generally from −100° C. to 200° C., preferably from −80° C. to 150° C., particularly preferably from 20° C. to 150° C. The temperature is selected so that at least one reactant is present in a liquid phase. The subsequent reaction temperature is in a preferred range from 20° C. to 150° C. Furthermore, the reaction can be carried out at atmospheric pressure but can also be carried out at superatmospheric pressure, although this requires appropriate reactors. The ratio in which the compounds of the formulae (V) and (VI) are combined, based on the amount of $M^3$ in the compounds of the formula (VI) used, is from 1:1000 to 1:0.01. Preference is given to a stoichiometric ratio of compounds of the formula (V) to amount of $M^3$ in the compounds of the formula (VI) used of from 1:100 to 1:0.1 Particular preference is given to a stoichiometric reaction based on the compounds of the formulae (V) and (VI).

The present invention further provides a novel chemical compound of the formula (VII-A)

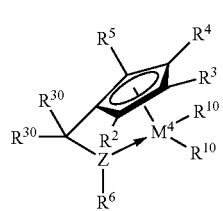

(VII-A)

$R^{30}$ is a hydrogen atom, $C_1$–$C_{18}$-alkyl such as methyl, ethyl, n-butyl, n-hexyl, tert-butyl, isopropyl, isobutyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl such as phenyl, tolyl, xylyl, $C_5$–$C_{18}$-heteroaryl such as furanyl, pyridinyl, $C_7$–$C_{20}$-arylalkyl, $C_7$–$C_{20}$alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably hydrogen, $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably hydrogen, methyl, ethyl, n-butyl, n-hexyl, tert-butyl, phenyl or tolyl, where the $R^{30}$ substituents do not both have the same meaning when Z=nitrogen and the $R^{30}$ substituents can both have the same meaning when Z=phosphorus, $R^2$, $R^3$, $R^4$, $R^5$ are identical or different and are each a hydrogen atom, $C_1$–$C_{18}$-alkyl such as methyl, ethyl, n-butyl, n-hexyl, tert-butyl, isopropyl, isobutyl, $C_3$–$C_{12}$ cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, isopropyl, isobutyl $C_6$–$C_{18}$-aryl such as phenyl, tolyl, xylyl, particularly preferably methyl, ethyl, n-butyl, n-hexyl, tert-butyl, phenyl or tolyl, where the radicals $R^2$, $R^3$, $R^4$ and $R^5$ may together form cyclic systems such as indenyls, benzindenyls, fluorenyl and phenanthryl which may in turn be substituted, $R^6$ is a hydrogen atom, $C_1$–$C_{18}$-alkyl such as methyl, ethyl, n-butyl, n-hexyl, isopropyl, isobutyl, $C_3$–$C_{12}$-cycloalkyl such as cyclopentyl, cyclohexyl or cyclooctyl, $C_2$–$C_{10}$-alkenyl, $C_3$–$C_{15}$-alkylalkenyl, $C_6$–$C_{18}$-aryl, $C_5$–$C_{18}$-heteroaryl such as furanyl, pyridinyl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, isopropyl, isobutyl, $C_6$–$C_{18}$-aryl such as phenyl, tolyl, xylyl, particularly preferably methyl, ethyl, cyclohexyl, n-butyl, n-hexyl, tert-butyl, phenyl or tolyl, $R^{10}$ is a hydrogen atom, a halogen atom, a $C_1$–$C_{20}$ group such as methyl, ethyl, propyl, isopropyl, isobutyl, $C_5$–$C_{20}$-aryl such as phenyl, tolyl, xylyl, $C_6$–$C_{20}$-aryloxy such as substituted or unsubstituted phenoxy and biphenoxy, $C_1$–$C_{20}$-alkyloxy, a nitrogen-containing compound, preferably fluorine or chlorine, methyl, ethyl, phenyl, substituted or unsubstituted phenoxy, NMe$_2$, NEt$_2$, very particularly preferably chlorine, NMe$_2$, NEt$_2$, Z is phosphorus, oxygen, nitrogen or sulfur, particularly preferably phosphorus, $M^4$ is an element of groups 3 to 8 of the Periodic Table of the Elements, particularly preferably titanium, zirconium, hafnium, vanadium, niobium, tantalum, chromium, molybdenum or tungsten, very particularly preferably titanium, zirconium or hafnium.

The dichloro and diamido compounds can be converted by literature methods into the corresponding butadiene complexes (EP-A-0687682) or bisphenol complexes (DE-A-19900732).

Nonlimiting examples of compounds of the formula VII or (VII-A) are:

bis(dimethylamido){η$^5$:κP-1-(P-tolylphosphido)-2,2-methylpropylidenecyclopentadienyl}titanium bis(dimethylamido){η$^5$:κP-1-(P-cyclohexylphosphido)-2,2-methylpropylidenecyclopentadienyl}titanium bis(dimethylamido){η$^5$:κP-1-(P-cyclohexylphosphido)-1-methylethylidenecyclopentadienyl}titanium bis(dimethylamido){η$^5$:κP-1-(P-cyclohexylphosphido)-1-methylethylidenecyclopentadienyl}zirconium bis(diethylamido){η$^5$:κP-1-(P-phenylphosphido)-ethylidenecyclopentadienyl}zirconium bis(diethylamido){η$^5$:κP-1-(P-phenylphosphido)-p-tolylmethylidenecyclopentadienyl}zirconium bis(diethylamido){η$^5$:κP-1-(P-tolylphosphido)-2,2-methylpropylidenecyclopentadienyl}zirconium bis(diethylamido){η$^5$:κP-1-(P-tert-butylphosphido)-2,2-methylpropylidenecyclopentadienyl}zirconium bis(diethylamido){η$^5$:κN-(P-tert-butylphosphido)methylidene-2,3,4,5-tetramethylcyclopentadienyl}-zirconium bischloro{η$^5$:κP-1-(P-tolylphosphido)-2,2-methylpropylidene-2,3,4,5-tetramethylcyclopentadienyl}titanium bischloro{η$^5$:κP-1-(P-phenylphosphido)ethylidene-2,3,4,5-tetramethylcyclopentadienyl}zirconium bischloro{η$^5$:κP-1-(P-phenylphosphido)-p-tolylmethylidene-2,3,4,5-tetramethylcyclopentadienyl}-zirconium bischloro{η$^5$:κP-1-(P-tolylphosphido)-2,2-methylpropylidene-2,3,4,5-tetramethylcyclopentadienyl}zirconium bischloro{η$^5$:κP-1-(P-tert-butylphosphido)-2,2-methylpropylidene-2,3,4,5-tetramethylcyclopentadienyl}-zirconium bischloro{η$^5$:κN-(P-tert-butylphosphido)methylidene-2,3,4,5-tetramethylcyclopentadienyl}zirconium bischloro{η$^5$:κP-1-(P-tolylphosphido)-2,2-methylpropylidenecyclopentadienyl}titanium bischloro{η$^5$:κP-1-(P-phenylphosphido)ethylidenecyclopentadienyl}zirconium bischloro{η$^5$:κP-1-(P-phenylphosphido)-p-tolylmethylidenecyclopentadienyl}zirconium bischloro{η$^5$:κP-1-(P-tolylphosphido)-2,2-methylpropylidenecyclopentadienyl}zirconium bischloro{η$^5$:κP-1-(P-tert-butylphosphido)-2,2-methylpropylidenecyclopentadienyl}zirconium bischloro{η$^5$:κP-(P-tert-butylphosphido)methylidene-2,3,4,5-tetramethylcyclopentadienyl}zirconium bischloro{η$^5$:κP-1-(P-cyclohexylphosphido)-2,2-methylpropylidenecyclopentadienyl}titanium bischloro{η$^5$:κP-1-(P-cyclohexylphosphido)ethylidenecyclopentadienyl}zirconium bischloro{η$^5$:κP-1-(P-cyclohexylphosphido)-p-tolylmethylidenecyclopentadienyl}zirconium bischloro{η$^5$:κP-1-(P-cyclohexylphosphido)-2,2-methylpropylidenecyclopentadienyl}zirconium bischloro{η$^5$:κP-1-(P-cyclohexylphosphido)-2,2-methylpropylidenecyclopentadienyl}zirconium bischloro{η$^5$:κP-(P-cyclohexylphosphido)methylidene-2,3,4,5-tetramethylcyclopentadienyl}zirconium bis(diethylamido){η⁵:κP-1-(P-tolylphosphido)-2,2-methylpropylidenecyclopentadienyl}titanium
bis(dimethylamido){η⁵:κP-1-(P-phenylphosphido)ethylidenecyclopentadienyl}zirconium
bis(dimethylamido){η⁵:κP-1-(P-phenylphosphido)-p-tolylmethylidenecyclopentadienyl}zirconium
bis(dimethylamido){η⁵:κP-1-(P-tolylphosphido)-2,2-methylpropylidenecyclopentadienyl}zirconium
bis(dimethylamido){η⁵:κP-1-(P-tert-butylphosphido)-2,2-methylpropylidenecyclopentadienyl}zirconium
bis(dimethylamido){η⁵:κP-(P-tert-butylphosphido)methylidene-2,3,4,5-tetramethylcyclopentadienyl}zirconium
bis(diethylamido){η⁵:κP-1-(P-tolylphosphido)-2,2-methylpropylidenecyclopentadienyl}hafnium
bis(dimethylamido){η⁵:κP-1-(P-phenylphosphido)ethylidenecyclopentadienyl}hafnium
bis(dimethylamido){η⁵:κP-1-(P-phenylphosphido)-p-tolyl-methylidenecyclopentadienyl}hafnium
bis(dimethylamido){η⁵:κP-1-(P-tolylphosphido)-2,2-methylpropylidenecyclopentadienyl}hafnium
bis(dimethylamido){η⁵:κP-1-(P-tert-butylphosphido)-2,2-methylpropylidenecyclopentadienyl}hafnium
bis(dimethylamido){η⁵:κN-(P-tert-butylphosphido)methylidene-2,3,4,5-tetramethylcyclopentadienyl}hafnium
bischloro{η⁵:κN-(P-tert-butylphosphido)methylidene-2,3,4,5-tetramethylcyclopentadienyl}hafnium
bischloro{η⁵:κP-1-(P-tolylphosphido)-2,2-methylpropylidenecyclopentadienyl}hafnium
bischloro{η⁵:κP-1-(P-phenylphosphido)ethylidenecyclopentadienyl}hafnium
bischloro{η⁵:κP-1-(P-phenylphosphido)-p-tolylmethylidenecyclopentadienyl}hafnium
bischloro{η⁵:κP-1-(P-tolylphosphido)-2,2-methylpropylidenecyclopentadienyl}hafnium
bischloro{η⁵:κP-1-(P-tert-butylphosphido)-2,2-methylpropylidenecyclopentadienyl}hafnium
bischloro{η⁵:κP-(P-tert-butylphosphidomethyl-2,3,4,5-tetramethylcyclopentadienyl}hafnium
bis(dimethylamido){η⁵:κP-1-(P-cyclohexylphosphido)-2,2-methylpropylidenecyclopentadienyl}hafnium
bis(dimethylamido){η⁵:κN-(P-cyclohexylphosphido)methylidene-2,3,4,5-tetramethylcyclopentadienyl}hafnium
bischloro{η⁵:κN-(P-cyclohexylphosphido)methylidene-2,3,4,5-tetramethylcyclopentadienyl}hafnium
bischloro{η⁵:κP-1-(P-cyclohexylphosphido)-2,2-methyl-propylidenecyclopentadienyl}hafnium
bischloro{η⁵:κP-1-(P-cyclohexylphosphido)ethylidenecyclopentadienyl}hafnium
bischloro{η⁵:κP-1-(P-cyclohexylphosphido)-p-tolylmethylidenecyclopentadienyl}hafnium
bischloro{η⁵:κP-1-(P-cyclohexylphosphido)-2,2-methyl-propylidenecyclopentadienyl}hafnium
bischloro{η⁵:κP-1-(P-cyclohexylphosphido)-2,2-methylpropylidenecyclopentadienyl}hafnium
bischloro{η⁵:κP-(P-cyclohexylphosphido)methylidene-2,3,4,5-tetramethylcyclopentadienyl}hafnium
(cis-η⁴-butadiene){η⁵:κP-1-(P-tolylphosphido)-2,2-methylpropylidenecyclopentadienyl}titanium
(cis-η⁴-butadiene){η⁵:κP-1-(P-phenylphosphido)ethylidenecyclopentadienyl}zirconium
(cis-η⁴-butadiene){η⁵:κP-1-(P-phenylphosphido)-p-tolylmethylidenecyclopentadienyl}zirconium
(cis-η⁴-butadiene){η⁵:κP-1-(P-tolylphosphido)-2,2-methylpropylidenecyclopentadienyl}zirconium
(cis-η⁴-butadiene){η⁵:κP-1-(P-tert-butylphosphido)-2,2-methylpropylidenecyclopentadienyl}zirconium
(cis-η⁴-butadiene){η⁵:κN-(P-tert-butylphosphido)methylidene-2,3,4,5-tetramethylcyclopentadienyl}zirconium
(cis-η⁴-butadiene){η⁵:κP-1-(P-tolylphosphido)-2,2-methylpropylidenecyclopentadienyl}hafnium
(cis-η⁴-butadiene){η⁵:κP-1-(P-phenylphosphido)ethylidenecyclopentadienyl}hafnium
(cis-η⁴-butadiene){η⁵:κP-1-(P-phenylphosphido)-p-tolylmethylidenecyclopentadienyl}hafnium
(cis-η⁴-butadiene){η⁵:κP-1-(P-tolylphosphido)-2,2-methylpropylidenecyclopentadienyl}hafnium
(cis-η⁴-butadiene){η⁵:κP-1-(P-tert-butylphosphido)-2,2-methylpropylidenecyclopentadienyl}hafnium
(cis-η⁴-butadiene){η⁵:κN-(P-tert-butylphosphido)methylidene-2,3,4,5-tetramethylcyclopentadienyl}hafnium
(trans-η⁴-butadiene){η⁵:κP-1-(P-tolylphosphido)-2,2-methylpropylidenecyclopentadienyl}titanium
(trans-η⁴-butadiene){η⁵:κP-1-(P-phenylphosphido)ethylidenecyclopentadienyl}zirconium
(trans-η⁴-butadiene){η⁵:κP-1-(P-phenylphosphido)-p-tolylmethylidenecyclopentadienyl}zirconium
(trans-η⁴-butadiene){η⁵:κP-1-(P-tolylphosphido)-2,2-methylpropylidenecyclopentadienyl}zirconium
(trans-η⁴-butadiene){η⁵:κP-1-(P-tert-butylphosphido)-2,2-methylpropylidenecyclopentadienyl}zirconium
(trans-η⁴-butadiene){η⁵:κP-(P-tert-butylphosphido)methylidene-2,3,4,5-tetramethylcyclopentadienyl}-zirconium
(trans-η⁴-butadiene){η⁵:κP-1-(P-tolylphosphido)-2,2-methylpropylidenecyclopentadienyl}hafnium
(trans-η⁴-butadiene){η⁵:κP-1-(P-phenylphosphido)ethylidenecyclopentadienyl}hafnium
(trans-η⁴-butadiene){η⁵:κP-1-(P-phenylphosphido)-p-tolylmethylidenecyclopentadienyl}hafnium
(trans-η⁴-butadiene){η⁵:κP-1-(P-tolylphosphido)-2,2-methylpropylidenecyclopentadienyl}hafnium
(trans-η⁴-butadiene){η⁵:κP-1-(P-tert-butylphosphido)-2,2-methylpropylidenecyclopentadienyl}hafnium
(trans-η⁴-butadiene){η⁵:κN-(P-tert-butylphosphido)methylidene-2,3,4,5-tetramethylcyclopentadienyl}hafnium
bis(phenolato){η⁴:κP-1-(P-tolylphosphido)-2,2-methylpropylidenecyclopentadienyl}titanium
bis(phenolato){η⁵:κP-1-(P-phenylphosphido)ethylcyclopentadienyl}zirconium
bis(phenolato){η⁵:κP-1-(P-phenylphosphido)-p-tolyl-methylidenecyclopentadienyl}zirconium
bis(phenolato){η⁵:κP-1-(P-tolylphosphido)-2,2-methylpropylidenecyclopentadienyl}zirconium
bis(phenolato){η⁵:κP-1-(P-tert-butylphosphido)-2,2-methylpropylidenecyclopentadienyl}zirconium
bis(phenolato){η⁵:κN-(P-tert-butylphosphido)methylidene-2,3,4,5-tetramethylcyclopentadienyl}zirconium
bis(dimethylamido){η⁵:κP-1-(P-tolylphosphido)isopropylmethylidenecyclopentadienyl}titanium
bis(diethylamido){η⁵:κP-1-(P-tolylphosphido)ethylidenecyclopentadienyl}zirconium
bis(diethylamido){η⁵:κP-1-(P-phenylphosphido)ethylmethylidenecyclopentadienyl}zirconium
bis(diethylamido){η⁵:κP-1-(P-tolylphosphido)cyclohexylmethylidenecyclopentadienyl}zirconium
bis(diethylamido){η⁵:κP-1-(P-tert-butylphosphido)cyclohexylmethylidenecyclopentadienyl}zirconium
bis(diethylamido){η⁵:κN-(P-tert-butylphosphido)-2,2-methylpropylidene-2,3,4,5-tetramethylcyclopentadienyl}zirconium
bis(dimethylamido){η⁵:κP-1-(P-tolylphosphido)isopropylmethylideneindenyl}titanium
bis(diethylamido){η⁵:κP-1-(P-tolylphosphido)ethylindenyl}zirconium bis(diethylamido){η⁵:κP-1-(P-phenylphosphido)
ethylmethylideneindenyl}zirconium
bis(diethylamido){η⁵:κP-1-(P-tolylphosphido)
cyclohexylmethylideneindenyl}zirconium
bis(diethylamido){η⁵:κP-1-(P-tert-butylphosphido)
cyclohexylmethylideneindenyl}zirconium
bis(dimethylamido){η⁵:κP-1-(P-tolylphosphido)isopropyl-
methylidene benzindenyl}titanium
bis(diethylamido){η⁵:κP-1-(P-tolylphosphido)
ethylidenebenzindenyl}zirconium
bis(diethylamido){η⁵:κP-1-(P-phenylphosphido)
ethylmethylidenebenzindenyl}zirconium
bis(diethylamido){η⁵:κP-1-(P-tolylphosphido)
cyclohexylmethylidenebenzindenyl}zirconium
bis(diethylamido){η⁵:κP-1-(P-tert-butylphosphido)
cyclohexylmethylidenebenzindenyl}zirconium
bis(dimethylamido){η⁵:κP-1-(P-tolylphosphido)
isopropylmethylidenefluorenyl}titanium
bis(diethylamido){η⁵:κP-1-(P-tolylphosphido)
ethylfluorenyl}zirconium
bis(diethylamido){η⁵:κP-1-(P-phenylphosphido)
ethylmethylidenefluorenyl}zirconium
bis(diethylamido){η⁵:κP-1-(P-tolylphosphido)
cyclohexylmethylidenefluorenyl}zirconium
bis(diethylamido){η⁵:κP-1-(P-tert-butylphosphido)
cyclohexylmethylidenefluorenyl}zirconium
bis(dimethylamido){η⁵:κP-1-(P-tolylphosphido)
isopropylmethylidenephenanthryl}titanium
bis(diethylamido){η⁵:κP-1-(P-tolylphosphido)
ethylidenephenanthryl}zirconium
bis(diethylamido){η⁵:κP-1-(P-phenylphosphido)
ethylmethylidenephenanthryl}zirconium
bis(diethylamido){η⁵:κP-1-(P-tolylphosphido)
cyclohexylmethylidenephenanthryl}zirconium
bis(diethylamido){η⁵:κP-1-(P-tert-butylphosphido)
cyclohexylmethylidenephenanthryl}zirconium
bis(dimethylamido){η⁵:κN-1-(N-tolylamido)-tert-
butylcyclopentadienyl}titanium
bis(diethylamido){η⁵:κN-1-(N-phenylamido)
ethylcyclopentadienyl}zirconium
bis(diethylamido){η⁵:κN-1-(N-phenylamido)-p-
tolylmethylcyclopentadienyl}zirconium
bis(diethylamido){η⁵:κN-1-(N-tolylamido)-tert-
butylmethylcyclopentadienyl}zirconium
bis(diethylamido){η⁵:κN-1-(N-tert-butylamido)-tert-
butylmethylcyclopentadienyl}zirconium
bis(diethylamido){η⁵:κN-1-(N-tert-butylamido)methyl-2,3,
4,5-tetramethylcyclopentadienyl}zirconium
bischloro{η⁵:κN-1-(N-tolylamido)-tert-butylmethyl-2,3,4,
5-tetramethylcyclopentadienyl}titanium
bischloro{η⁵:κN-1-(N-phenylamido)ethyl-2,3,4,5-
tetramethylcyclopentadienyl}zirconium
bischloro{η⁵:κN-1-(N-phenylamido)-p-tolylmethyl-2,3,4,
5-tetramethylcyclopentadienyl}zirconium
bischloro{η⁵:κN-1-(N-tolylamido)-tert-butylmethyl-2,3,4,
5-tetramethylcyclopentadienyl}zirconium
bischloro{η⁵:κN-1-(N-tert-butylamido)-tert-butylmethyl-2,
3,4,5-tetramethylcyclopentadienyl}zirconium
bischloro{η⁵:κN-1-(N-tert-butylamidomethyl-2,3,4,5-
tetramethylcyclopentadienyl}zirconium
bischloro{η⁵:κN-1-(N-tolylamido)-tert-
butylmethylcyclopentadienyl}titanium
bischloro{η⁵:κN-1-(N-phenylamido)
ethylcyclopentadienyl}zirconium
bischloro{η⁵:κN-1-(N-phenylamido)-p-
tolylmethylcyclopentadienyl}zirconium
bischloro{η⁵:κN-1-(N-tolylamido)-tert-
butylmethylcyclopentadienyl}zirconium
bischloro{η⁵:κN-1-(N-tert-butylamido)-tert-
butylmethylcyclopentadienyl}zirconium
bischloro{η⁵:κN-1-(N-tert-butylamidomethyl-2,3,4,5-
tetramethylcyclopentadienyl}zirconium
bis(diethylamido){η⁵:κN-1-(N-tolylamido)-tert-
butylmethylcyclopentadienyl}titanium
bis(dimethylamido){η⁵:κN-1-(N-phenylamido)
ethylcyclopentadienyl}zirconium
bis(dimethylamido){η⁵:κN-1-(N-phenylamido)-p-
tolylmethylcyclopentadienyl}zirconium
bis(dimethylamido){η⁵:κN-1-(N-tolylamido)-tert-
butylmethylcyclopentadienyl}zirconium
bis(dimethylamido){η⁵:κN-1-(N-tert-butylamido)-tert-
butylmethylcyclopentadienyl}zirconium
bis(dimethylamido){η⁵:κN-1-(N-tert-butylamido)methyl-2,
3,4,5-tetramethylcyclopentadienyl}zirconium
bis(diethylamido){η⁵:κN-1-(N-tolylamido)-tert-
butylmethylcyclopentadienyl}hafnium
bis(dimethylamido){η⁵:κN-1-(N-phenylamido)
ethylcyclopentadienyl}hafnium
bis(dimethylamido){η⁵:κN-1-(N-phenylamido)-p-
tolylmethylcyclopentadienyl}hafnium
bis(dimethylamido){η⁵:κN-1-(N-tolylamido)-tert-
butylmethylcyclopentadienyl}hafnium
bis(dimethylamido){η⁵:κN-1-(N-tert-butylamido)-tert-
butylmethylcyclopentadienyl}hafnium
bis(dimethylamido){η⁵:κN-1-(N-tert-butylamido)methyl)-
2,3,4,5-tetramethylcyclopentadienyl}hafnium
bischloro{η⁵:κN-1-(N-tert-butylamidomethyl-2,3,4,5-
tetramethylcyclopentadienyl}hafnium
bischloro{η⁵:κN-1-(N-tolylamido)-tert-
butylmethylcyclopentadienyl}hafnium
bischloro{η⁵:κN-1-(N-phenylamido)
ethylcyclopentadienyl}hafnium
bischloro{η⁵:κN-1-(N-phenylamido)-p-
tolylmethylcyclopentadienyl}hafnium
bischloro{η⁵:κN-1-(N-tolylamido)-tert-
butylmethylcyclopentadienyl}hafnium
bischloro{η⁵:κN-1-(N-tert-butylamido)-tert-
butylmethylcyclopentadienyl}hafnium
bischloro{η⁵:κN-1-(N-tert-butylamidomethyl-2,3,4,5-
tetramethylcyclopentadienyl}hafnium
(cis-η⁴-butadiene){η⁵:κN-1-(N-tolylamido)-tert-
butylmethylcyclopentadienyl}titanium
(cis-η⁴-butadiene){η⁵:κN-1-(N-phenylamido)
ethylcyclopentadienyl}zirconium
(cis-η⁴-butadiene){η⁵:κN-1-(N-phenylamido)-p-
tolylmethylcyclopentadienyl}zirconium
(cis-η⁴-butadiene){η⁵:κN-1-(N-tolylamido)-tert-
butylmethylcyclopentadienyl}zirconium
(cis-η⁴-butadiene){η⁵:κN-1-(N-tert-butylamido)-tert-
butylmethylcyclopentadienyl}zirconium
(cis-η⁴-butadiene){η⁵:κN-1-(N-tert-butylamido)methyl-2,
3,4,5-tetramethylcyclopentadienyl}zirconium
(cis-η⁴-butadiene){η⁵:κN-1-(N-tolylamido)-tert-
butylmethylcyclopentadienyl}hafnium
(cis-η⁴-butadiene){η⁵:κN-1-(N-phenylamido)
ethylcyclopentadienyl}hafnium
(cis-η⁴-butadiene){η⁵:κN-1-(N-phenylamido)-p-
tolylmethylcyclopentadienyl}hafnium
(cis-η⁴-butadiene){η⁵:κN-1-(N-tolylamido)-tert-
butylmethylcyclopentadienyl}hafnium
(cis-η⁴-butadiene){η⁵:κN-1-(N-tert-butylamido)-tert-
butylmethylcyclopentadienyl}hafnium (cis-η⁴-butadiene){η⁵:κN-1-(N-tert-butylamido)methyl-2,3,4,5-tetramethylcyclopentadienyl}hafnium
(trans-η⁴-butadiene){η⁵:κN-1-(N-tolylamido)-tert-butylmethylcyclopentadienyl}titanium
(trans-η⁴-butadiene){η⁵:κN-1-(N-phenylamido)ethylcyclopentadienyl}zirconium
(trans-η⁴-butadiene){η⁵:κN-1-(N-phenylamido)-p-tolylmethylcyclopentadienyl}zirconium
(trans-η⁴-butadiene){η⁵:κN-1-(N-tolylamido)-tert-butylmethylcyclopentadienyl}zirconium
(trans-η⁴-butadiene){η⁵:κN-1-(N-tert-butylamido)-tert-butylmethylcyclopentadienyl}zirconium
(trans-η⁴-butadiene){η⁵:κN-1-(N-tert-butylamido)methyl-2,3,4,5-tetramethylcyclopentadienyl}zirconium
(trans-η⁴-butadiene){η⁵:κN-1-(N-tolylamido)-tert-butylmethylcyclopentadienyl}hafnium
(trans-η⁴-butadiene){η⁵:κN-1-(N-phenylamido)ethylcyclopentadienyl}hafnium
(trans-η⁴-butadiene){η⁵:κN-1-(N-phenylamido)-p-tolylmethylcyclopentadienyl}hafnium
(trans-η⁴-butadiene){η⁵:κN-1-(N-tolylamido)-tert-butylmethylcyclopentadienyl}hafnium
(trans-η⁴-butadiene){η⁵:κN-1-(N-tert-butylamido)-tert-butylmethylcyclopentadienyl}hafnium
(trans-η⁴-butadiene){η⁵:κN-1-(N-tert-butylamido)methyl-2,3,4,5-tetramethylcyclopentadienyl}hafnium
bis(phenolato){η⁵:κN-1-(N-tolylamido)-tert-butylmethylcyclopentadienyl}titanium
bis(phenolato){η⁵:κN-1-(N-phenylamido)ethylcyclopentadienyl}zirconium
bis(phenolato){η⁵:κN-1-(N-phenylamido)-p-tolylmethylcyclopentadienyl}zirconium
bis(phenolato){η⁵:κN-1-(N-tolylamido)-tert-butylmethylcyclopentadienyl}zirconium
bis(phenolato){η⁵:κN-1-(N-tert-butylamido)-tert-butylmethylcyclopentadienyl}zirconium
bis(phenolato){η⁵:κN-1-(N-tert-butylamido)methyl-2,3,4,5-tetramethylcyclopentadienyl}zirconium
bis(dimethylamido){η⁵:κN-1-(N-tolylamido)isopropylmethylcyclopentadienyl}titanium
bis(diethylamido){η⁵:κN-1-(N-tolylamido)ethylcyclopentadienyl}zirconium
bis(diethylamido){η⁵:κN-1-(N-phenylamido)ethylmethylcyclopentadienyl}zirconium
bis(diethylamido){η⁵:κN-1-(N-tolylamido)cyclohexylmethylcyclopentadienyl}zirconium
bis(diethylamido){η⁵:κN-1-(N-tert-butylamido)cyclohexylmethylcyclopentadienyl}zirconium
bis(diethylamido){η⁵:κN-1-(N-tert-butylamido)-tert-butylmethyl-2,3,4,5-tetramethylcyclopentadienyl}zirconium
bis(dimethylamido){η⁵:κN-1-(N-tolylamido)isopropylmethylindenyl}titanium
bis(diethylamido){η⁵:κN-1-(N-tolylamido)ethylindenyl}zirconium
bis(diethylamido){η⁵:κN-1-(N-phenylamido)ethylmethylindenyl}zirconium
bis(diethylamido){η⁵:κN-1-(N-tolylamido)cyclohexylmethylindenyl}zirconium
bis(diethylamido){η⁵:κN-1-(N-tert-butylamido)cyclohexylmethylindenyl}zirconium
bis(dimethylamido){η⁵:κN-1-(N-tolylamido)isopropylmethylbenzindenyl}titanium
bis(diethylamido){η⁵:κN-1-(N-tolylamido)ethylbenzindenyl}zirconium
bis(diethylamido){η⁵:κN-1-(N-phenylamido)ethylmethylbenzindenyl}zirconium
bis(diethylamido){η⁵:κN-1-(N-tolylamido)cyclohexylmethylbenzindenyl}zirconium
bis(diethylamido){η⁵:κN-1-(N-tert-butylamido)cyclohexylmethylbenzindenyl}zirconium
bis(dimethylamido){η⁵:κN-1-(N-tolylamido)isopropylmethylfluorenyl}titanium
bis(diethylamido){η⁵:κN-1-(N-tolylamido)ethylfluorenyl}zirconium
bis(diethylamido){η⁵:κN-1-(N-phenylamido)ethylmethylfluorenyl}zirconium
bis(diethylamido){η⁵:κN-1-(N-tolylamido)cyclohexylmethylfluorenyl}zirconium
bis(diethylamido){η⁵:κN-1-(N-tert-butylamido)cyclohexylmethylfluorenyl}zirconium
bis(dimethylamido){η⁵:κN-1-(N-tolylamido)isopropylmethylphenanthryl}titanium
bis(diethylamido){η⁵:κN-1-(N-tolylamido)ethylphenanthryl}zirconium
bis(diethylamido){η⁵:κN-1-(N-phenylamido)ethylmethylphenanthryl}zirconium
bis(diethylamido){η¹⁵:κN-1-(N-tolylamido)cyclohexylmethylphenanthryl}zirconium
bis(diethylamido){η⁵:κN-1-(N-tert-butylamido)cyclohexylmethylphenanthryl}zirconium The present invention also provides a catalyst system comprising the chemical compound of the formula VII obtainable according to the present invention.

The metal complexes of the formula VII are particularly suitable as constituents of catalyst systems for preparing polyolefins by polymerization of at least one olefin in the presence of a catalyst comprising at least one cocatalyst and at least one metal complex.

The cocatalyst, which together with a transition metal complex of the formula VII forms the catalyst system, comprises at least one compound such as an aluminoxane or a Lewis acid or an ionic compound which reacts with metallocene to convert it into a cationic compound.

As aluminoxane, preference is given to using a compound of the formula (XI)

$$(R\,AlO)_n \qquad (XI)$$

Further suitable aluminoxanes may be, for example, cyclic as in formula (XII)

(XII)

or linear as in formula (XIII)

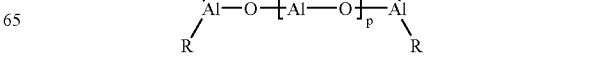

(XIII)

or of the cluster type as in formula (XIV)

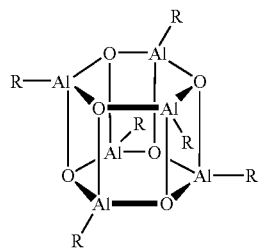

(XIV)

Such aluminoxanes are described, for example, in JACS 117 (1995), 6465–74, Organometallics 13 (1994), 2957–2969.

The radicals R in the formulae (XI), (XII), (XIII) and (XIV) may be identical or different and can each be a $C_1$–$C_{20}$-hydrocarbon group such as a $C_1$–$C_6$-alkyl group, a $C_6$–$C_{18}$-aryl group, benzyl or hydrogen, and p is an integer from 2 to 50, preferably from 10 to 35.

The radicals R are preferably identical and are each methyl, isobutyl, n-butyl, phenyl or benzyl, particularly preferably methyl.

If the radicals R are different, they are preferably methyl and hydrogen, methyl and isobutyl or methyl and n-butyl, with the hydrogen or isobutyl or n-butyl preferably being present in an amount of 0.01–40% (number of radicals R).

The aluminoxane can be prepared in various ways by known methods. One of the methods is, for example, to react an aluminum-hydrocarbon compound and/or a hydridoaluminum-hydrocarbon compound with water (gaseous, solid, liquid or bound—for example as water of crystallization) in an inert solvent (e.g. toluene)

To prepare an aluminoxane having different alkyl groups R, two different trialkylaluminums ($AlR_3$+$AlR'_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form or as adduct.

As Lewis acid, preference is given to using at least one organoboron or organoaluminum compound containing $C_1$–$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl, p-fluorophenyl, 3,5-difluorophenyl, pentachlorophenyl, pentafluorophenyl, 3,4,5-trifluorophenyl or 3,5-di(trifluoromethyl)phenyl.

Examples of Lewis acids are trimethylaluminium, triethylaluminium, triisobutylaluminium, tributylaluminium, trifluoroborane, triphenylborane, tris(4-fluorophenyl)borane, tris(3,5-difluorophenyl)borane, tris(4-fluoromethylphenyl) borane, tris(pentafluorophenyl)borane, tris(tolyl)borane, tris (3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to compounds which contain a noncoordinating anion, for example tetrakis (pentafluorophenyl)borate, tetraphenylborate, $SbF_6^-$, $CF_3SO_3^-$ or $ClO_4^-$. Cationic counterions used are protonated Lewis bases such as methylamine, aniline, N,N-dimethylbenzylamine and its derivatives, N,N-dimethylcyclohexylamine and its derivatives, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene or triphenylcarbenium.

Examples of such ionic compounds are
triethylammonium tetra(phenyl)borate,
tributylammonium tetra(phenyl)borate,
trimethylammonium tetra(tolyl)borate,
tributylammonium tetra(tolyl)borate,
tributylammonium tetra(pentafluorophenyl)borate,
tributylammonium tetra(pentafluorophenyl)aluminate,
tripropylammonium tetra(dimethylphenyl)borate,
tributylammonium tetra (trifluoromethylphenyl)borate,
tributylammonium tetra(4-fluorophenyl)borate,
N,N-dimethylanilinium tetra(phenyl)borate,
N,N-diethylanilinium tetra(phenyl)borate,
N,N-dimethylanilinium tetrakis(pentafluorophenyl)borate,
N,N-dimethylanilinium tetrakis(pentafluorophenyl)aluminate,
di(propyl)ammonium tetrakis(pentafluorophenyl)borate,
di(cyclohexyl)ammonium tetrakis(pentafluorophenyl)borate,
triphenylphosphonium tetrakis(phenyl)borate,
triethylphosphonium tetrakis(phenyl)borate,
N,N-dimethylcyclohexylammonium tetrakis(pentafluorophenyl)borate
N,N-dimethylbenzylammonium tetrakis(pentafluorophenyl) borate
diphenylphosphonium tetrakis(phenyl)borate,
tri(methylphenyl)phosphonium tetrakis(phenyl)borate,
tri(dimethylphenyl)phosphonium tetrakis(phenyl)borate,
triphenylcarbenium tetrakis(pentafluorophenyl)borate,
triphenylcarbenium tetrakis(pentafluorophenyl)aluminate,
triphenylcarbenium tetrakis(phenyl)aluminate,
ferrocenium tetrakis(pentafluorophenyl)borate and/or
ferrocenium tetrakis(pentafluorophenyl)aluminate.

Triphenylcarbenium tetrakis(pentafluorophenyl)borate and/or N,N-dimethylanilinium tetrakis(pentafluorophenyl) borate are preferred.

It is also possible to use mixtures of a Lewis acid and at least one ionic compound.

Further suitable cocatalyst components are borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammonium undecahydrido-8-ethyl-7,9-dicarbaundecaborate,
4-carbanonaborane(14),
bis(tri(butyl)ammonium)nonaborate,
bis(tri(butyl)ammonium)undecaborate,
bis(tri(butyl)ammonium)dodecaborate,
bis(tri(butyl)ammonium)decachlorodecaborate,
tri(butyl)ammonium 1-carbadecaborate,
tri(butyl)ammonium 1-carbadodecaborate,
tri(butyl)ammonium 1-trimethylsilyl-1-carbadecaborate,
tri(butyl)ammonium bis(nonahydrido-1,3-dicarbanonaborato)cobaltate(III),
tri(butyl)ammonium bis(undecahydrido-7,8-dicarbaundecaborato)ferrate(III).

Cocatalyst systems which are likewise useful are combinations of at least one of the abovementioned amines and a support with organoelement compounds as described in WO 99/40129.

Preferred constituents of these cocatalyst systems are compounds of the formulae (A) and (B),

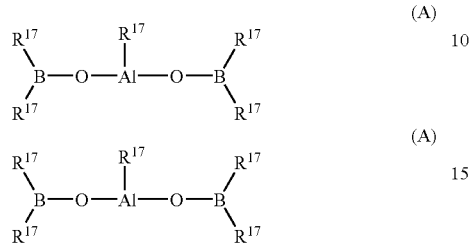

where
$R^{17}$ is a hydrogen atom, a halogen atom or a $C_1$–$C_{40}$ group, in particular $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{17}$ can also be an —$OSiR_3$ group, where R are identical or different and are as defined for $R^{17}$.

Further preferred cocatalysts are compounds in general which are formed by reaction of at least one compound of the formula (C) and/or (D) and/or (E) with at least one compound of the formula (F), $R^{17}{}_vB$-$(DR^{70})_s$      (C)

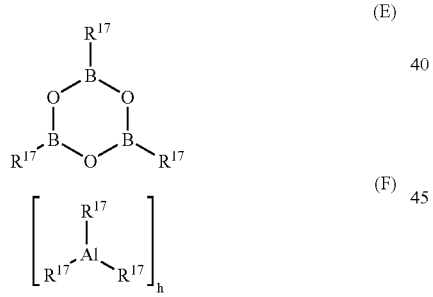

where
$R^{70}$ can be a hydrogen atom or a boron-free $C_1$–$C_{40}$-group such as $C_1$–$C_{20}$-alkyl, $C_6$–$C_{20}$-aryl, $C_7$–$C_{40}$-arylalkyl, $C_7$–$C_{40}$-alkylaryl, and
$R^{17}$ is as defined above,
$X^1$ is an element of group 14 of the Periodic Table of the Elements or an NR group, where R is a hydrogen atom or a $C_1$–$C_{20}$-hydrocarbon radical, such as $C_1$–$C_{20}$-alkyl or $C_1$–$C_{20}$-aryl,
D is an element of group 14 of the Periodic Table of the Elements or an NR group, where R is a hydrogen atom or a $C_1$–$C_{20}$-hydrocarbon radical such as $C_1$–$C_{20}$-alkyl or $C_1$–$C_{20}$-aryl,
v is an integer from 0 to 3,
s is an integer from 0 to 3,
h is an integer from 1 to 10.

If desired, the organoelement compounds are combined with an organometallic compound of the formula XI to XIV and/or XV $[M^{40}R^{19}{}_b]_d$, where $M^{40}$ is an element of group 1, 2 or 11 of the Periodic Table of the Elements, $R^{19}$ are identical or different and are each a hydrogen atom, a halogen atom or a $C_1$–$C_{40}$ group, in particular $C_1$–$C_{20}$-alkyl, $C_6$–$C_{40}$-aryl, $C_7$–$C_{40}$-arylalkyl or $C_7$–$C_{40}$-alkylaryl, b is an integer from 1 to 3 and d is an integer from 1 to 4.

Examples of cocatalytically active compounds of the formulae A and B are

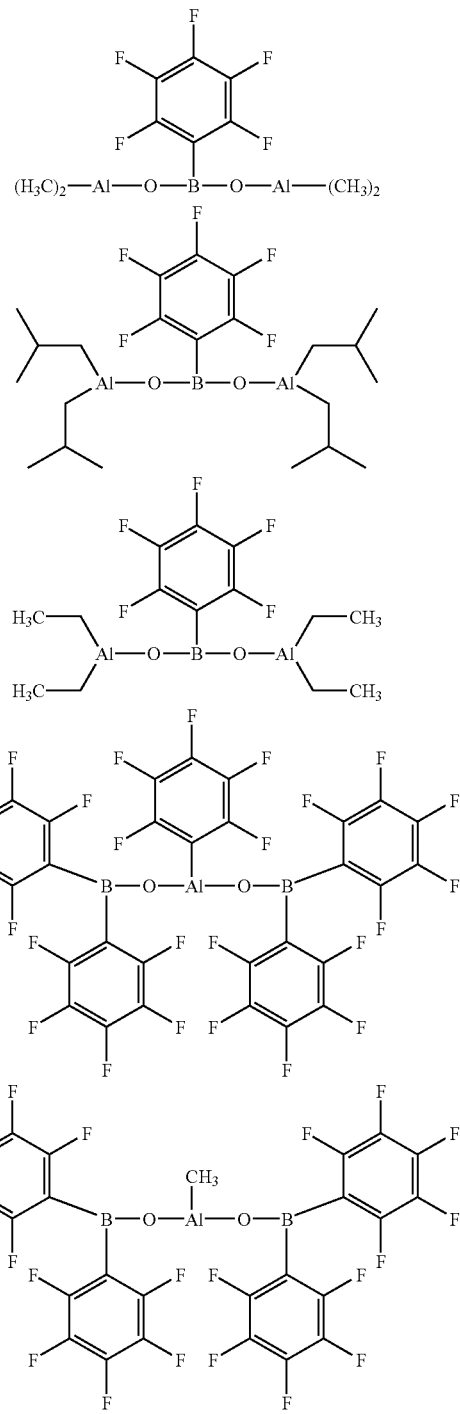

-continued

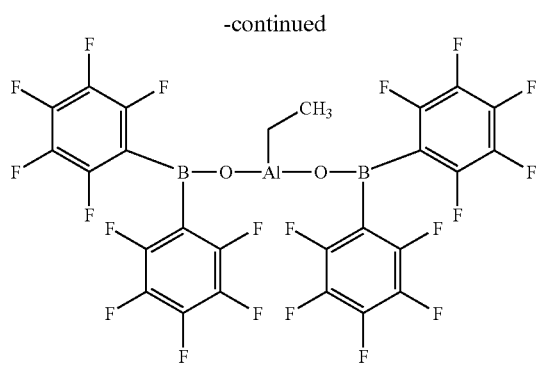

The organometallic compounds of the formula XV are preferably uncharged Lewis acids in which $M^{40}$ is lithium, magnesium and/or aluminum, in particular aluminum. Examples of preferred organometallic compounds of the formula XII are trimethylaluminum, triethylaluminum, triisopropylaluminum, trihexylaluminum, trioctylaluminum, tri-n-butylaluminum, tri-n-propylaluminum, triisoprenylaluminum, dimethylaluminum monochloride, diethylaluminum monochloride, diisobutylaluminum monochloride, methylaluminum sesquichloride, ethylaluminum sesquichloride, dimethylaluminumhydride, diethylaluminum hydride, diisopropylaluminum hydride, dimethylaluminum trimethylsiloxide, dimethylaluminum triethylsiloxide, phenylalane, pentafluorophenylalane and o-tolylalane.

Further cocatalysts which can be used in unsupported or supported form are the compounds mentioned in EP-A-924223, DE-A-19622207, EP-A-601830, EP-A-824112, EP-A-824113, EP-A-811627, WO97/11775 and DE-A-19606167.

The support component of the catalyst system of the present invention can be any organic or inorganic, inert solid, in particular a porous support such as talc, inorganic oxides and finely divided polymer powders (e.g. polyolefins).

Suitable inorganic oxides may be found among oxides of elements of groups 2, 11, 12, 13 and 14 and groups 3–9 of the Periodic Table of the Elements. Examples of oxides preferred as supports include silicon dioxide, aluminum oxide and also mixed oxides of the elements calcium, aluminum, silicon, magnesium, titanium and corresponding oxide mixtures. Other inorganic oxides which can be used alone or in combination with the abovementioned preferred oxidic supports are, for example, MgO, $ZrO_2$, $TiO_2$ or $B_2O_3$, to name only a few.

The support materials used generally have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, for example when using silica gel as support material, dehydration or drying is advisable. Thermal dehydration or drying of the support material can be carried out under reduced pressure with simultaneous inert gas blanketing (e.g. nitrogen). The drying temperature is in the range from 100 to 1000° C., preferably from 200 to 800° C. In this case, the parameter pressure is not critical. The duration of the drying process can be from 1 to 24 hours. Shorter or longer drying times are possible, provided that equilibrium with the hydroxyl groups on the support surface can be established under the conditions chosen, which normally takes from 4 to 8 hours.

Dehydration or drying of the support material can also be carried out by chemical means, by reacting the adsorbed water and the hydroxyl groups on the surface with suitable passivating agents. Reaction with the passivating reagent can convert all or some of the hydroxyl groups into a form which leads to no adverse interaction with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out by, for example, reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are possible. The reaction time is from 30 minutes to 20 hours, preferably from 1 to 5 hours. After chemical dehydration is complete, the support material is isolated by filtration under inert conditions, washed one or more times with suitable inert solvents such as those described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

To prepare the supported catalyst system, at least one of the above-described transition metal compounds of the formula VII is brought into contact in a suitable solvent with at least one cocatalyst component, preferably giving a soluble reaction product, an adduct or a mixture.

The composition obtained in this way is then mixed with the dehydrated or passivated support material, the solvent is removed and the resulting supported catalyst system comprising the transition metal compound is dried to ensure that all or most of the solvent has been removed from the pores of the support material. The supported catalyst is obtained as a free-flowing powder.

A process for preparing a free-flowing and possibly prepolymerized catalyst system comprising a transition metal compound comprises the following steps:

a) preparation of a transition metal compound/cocatalyst mixture in a suitable solvent or suspension medium, where the transition metal compound has one of the structures described above, b) application of the transition metal compound/cocatalyst mixture to a porous, preferably inorganic, dehydrated support, c) removal of the major part of the solvent from the resulting mixture, d) isolation of the supported catalyst system, e) if desired, prepolymerization of the resulting supported catalyst system using one or more olefinic monomer(s) to obtain a prepolymerized supported catalyst system.

Preferred solvents for the preparation of the transition metal compound/cocatalyst mixture are hydrocarbons and hydrocarbon mixtures which are liquid at the reaction temperature chosen and in which the individual components preferably dissolve. However, solubility of the individual components is not a prerequisite, as long as it is ensured that the reaction product of transition metal compound and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and transition metal compound used in the preparation of the supported catalyst system can be varied within a wide range. Preference is given to a molar ratio of aluminum to transition metal in the transition metal compounds of from 10:1 to 1000:1, very particularly preferably from 50:1 to 500:1.

In the case of methylaluminoxane, preference is given to using 30% strength solutions in toluene, but the use of 10% strength solutions is also possible.

For preactivation, the transition metal compound in the form of a solid is dissolved in a solution of the aluminoxane in a suitable solvent. However, it is also possible to dissolve the transition metal compound separately in a suitable solvent and subsequently to combine this solution with the aluminoxane solution. Preference is given to using toluene.

The preactivation time is from 1 minute to 200 hours.

The preactivation can take place at room temperature (25° C.). Use of higher temperatures can in some cases reduce the preactivation time required and can give an additional increase in activity. In this case, higher temperatures means a range from 50 to 100° C.

The preactivated solution or transition metal compound/cocatalyst mixture is subsequently combined with an inert support material, usually silica gel, which is present in the form of a dry powder or as a suspension in one of the abovementioned solvents. The support material is preferably used as powder. The order of addition is immaterial. The preactivated transition metal compound/cocatalyst solution or the transition metal compound/cocatalyst mixture can be added to the support material or else the support material can be introduced into the solution.

The volume of the preactivated solution or transition metal compound/cocatalyst mixture can exceed 100% of the total pore volume of the support material used or else can be up to 100% of the total pore volume.

The temperature at which the preactivated solution or transition metal compound/cocatalyst mixture is brought into contact with the support material can vary in a range from 0 to 100° C. However, lower or higher temperatures are also possible.

All or most of the solvent is subsequently removed from the supported catalyst system, during which the mixture can be stirred and, if desired, also heated. Preference is given to removing both the visible proportion of the solvent and the proportion present in the pores of the support material. The removal of the solvent can be carried out in a conventional way using reduced pressure and/or flushing with inert gas. During the drying procedure, the mixture can be heated until the free solvent has been removed, which usually takes from 1 to 3 hours at a preferred temperature of from 30 to 60° C.

The free solvent is the visible proportion of solvent in the mixture. Residual solvent is the proportion enclosed in the pores.

As an alternative to complete removal of the solvent, it is also possible to dry the supported catalyst system only to a certain residual solvent content, with the free solvent having been completely removed. The supported catalyst system can subsequently be washed with a low-boiling hydrocarbon such as pentane or hexane and dried again.

The supported catalyst system prepared according to the present invention can either be used directly for the polymerization of olefins or can be prepolymerized using one or more olefinic monomers prior to use in a polymerization process. The prepolymerization of supported catalyst systems is described, for example, in WO 94/28034.

As additive, it is possible to add a small amount of an olefin, preferably an α-olefin (for example vinylcyclohexane, styrene or phenyldimethylvinylsilane) as modifying component or an antistatic (as described in U.S. Ser. No. 08/365280) during or after the preparation of the supported catalyst system. The molar ratio of additive to the metallocene component (compound VII) is preferably from 1:1000 to 1000:1, very particularly preferably from 1:20 to 20:1.

The present invention also relates to a process for preparing a polyolefin by polymerization of one or more olefins in the presence of the novel catalyst system comprising at least one transition metal component of the formula VII. For the purposes of the present invention, the term polymerization encompasses both homopolymerization and copolymerization.

Preference is given to polymerizing olefins of the formula $R_m$—CH=CH—$R_n$, where $R_m$ and $R_n$ are identical or different and are each a hydrogen atom or a carbon-containing radical having from 1 to 20 carbon atoms, in particular from 1 to 10 carbon atoms, and $R_m$ and $R_n$ together with the atoms connecting them may form one or more rings.

Examples of such olefins are 1-olefins having 2–20 carbon atoms, preferably from 2 to 10 carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene, and cyclic olefins such as norbornene, tetracyclododecene or methylnorbornene. In the process of the present invention, preference is given to homopolymerizing ethene or propene or copolymerizing propene with ethene and/or with one or more 1-olefins having from 4 to 20 carbon atoms, e.g. butene, hexene, styrene or vinylcyclohexane, and/or one or more dienes having from 4 to 20 carbon atoms, e.g. 1,4-butadiene, norbornadiene, ethylidenenorbornene or ethylnorbornadiene. Examples of such copolymers are ethene-propene copolymers, ethene-norbornene, ethene-styrene or ethene-propene-1,4-hexadiene terpolymers.

The polymerization is generally carried out at from 0 to 300° C., preferably from 50 to 200° C., very particularly preferably 50–80° C. The pressure is generally from 0.5 to 2000 bar, preferably from 5 to 64 bar.

The polymerization can be carried out in solution, in bulk, in suspension or in the gas phase, continuously or batchwise, in one or more stages.

The catalyst system prepared according to the present invention can be used as sole catalyst component for the polymerization of olefins having from 2 to 20 carbon atoms, but is preferably used in combination with at least one alkyl compound of elements of main groups I to III of the Periodic Table, e.g. an aluminum, magnesium or lithium alkyl or an aluminoxane. The alkyl compound is added to the monomer or suspension medium and serves to free the monomer of substances which can impair the catalyst activity. The amount of alkyl compound added depends on the quality of the monomers used.

As molar mass regulator and/or to increase the activity, hydrogen can be added if required.

The catalyst system can be introduced into the polymerization system in pure form or can be admixed with inert components such as paraffins, oils or waxes to make it easier to meter. Furthermore, an antistatic can be introduced into the polymerization system either together with or separately from the catalyst system used.

The polymers prepared using the catalyst system of the present invention display a uniform particle morphology and contain no fines. No deposits or cake material occur in the polymerization using the catalyst system of the present invention.

The copolymers obtained using the catalyst system of the present invention can be produced with high productivity at industrially relevant process parameters without deposit formation. Copolymers having a high comonomer content and a high molar mass can be prepared using this catalyst system.

The invention is illustrated by the following nonlimiting examples.

EXAMPLES

General Procedures: preparation and handling of organometallic compounds was carried out in the absence of air and moisture under argon (Schlenk technique or Glove Box). All solvents required were purged with argon and dried over molecular sieves before use.

1,2,3,4-tetramethylfulvene (1)

2.00 g (0.014 mol) of pentamethylcyclopentadienyllithium (6) and 3.50 g (0.013 mol) of chlorotriphenylmethane are suspended at 0° C. in a 1:1 solvent mixture of 50.0 ml of toluene and 50 ml of tetrahydrofuran. The solution is stirred overnight at 5° C., giving a bright red reaction mixture. The suspension is subsequently evaporated to about 20.0 ml and admixed with 75.0 ml of pentane, resulting in precipitation of the lithium chloride formed in the reaction. The precipitate is filtered off to give a clear, bright orange solution. To remove the triphenylmethane formed in the reaction, the reaction solution is evaporated to half its volume and stored at −30° C. for 2 days. This results in precipitation of the triphenylmethane as a colorless, crystalline solid which can be separated off by decantation of the supernatant solution of 1,2,3,4-tetramethylfulvene (1). Residual pentane and tetrahydrofuran are subsequently removed at 0° C. in an oil pump vacuum to give a toluene solution of the orange product. Owing to the thermolability of the fulvene (1), complete isolation of the product is not carried out. To determine the yield or concentration of the compound (1) present in solution, the methyl group signal of the toluene in the $^1$H-NMR spectrum is integrated and compared to the integrated signals of the methyl groups of the tetramethylfulvene (1). The proportion by mass of the desired fulvene (1) can be determined from this ratio.

Yield: about 1.50 g (about 86%)

6,6-dimethylfulvene (2)

15.0 ml (12.0 g, 0.21 mol) of acetone and 41.0 ml (0.50 mol) of freshly distilled cyclopentadiene are dissolved in 80.0 ml of degassed methanol, after which 25.0 ml (0.30 mol) of pyrrolidine are added dropwise while cooling in ice. The reaction mixture is stirred while cooling in ice during the distinctly exothermic reaction. For the work-up, the mixture is neutralized with 18.0 ml of glacial acetic acid (pH monitoring) and 50.0 ml of water and 50.0 ml of diethyl ether are added. The phases are separated from one another, the aqueous phase is extracted three times with 50.0 ml each time of diethyl ether and the combined organic phases are washed firstly with 40.0 ml of water and then with 40.0 ml of saturated sodium chloride solution and dried over magnesium sulfate. The reaction solution is evaporated to about 50.0 ml on a rotary evaporator and the remaining ether is then removed by means of an oil pump while cooling in ice. The product is obtained as a yellow-orange liquid.

Yield: 15.0 g (70%) (lit.: 81%)

Lithium cyclohexylphosphide (3)

60.0 ml (34.8 mmol) of a 0.58 molar cyclohexylphosphine solution in hexane are dissolved in 100 ml of pentane and cooled to −78° C. 21.8 ml (34.9 mmol) of n-butyllithium solution are slowly added dropwise to this solution while stirring. The reaction mixture is warmed to room temperature overnight and the precipitated colorless lithium salt is subsequently isolated on a frit. The product is washed three times with 20 ml each time of pentane and then dried under reduced pressure.

Yield: 3.71 g (87%)

(Cyclohexylphosphinomethyl)tetramethylcyclopentadienyllithium (4)

200 mg (2.20 mmol) of lithium cyclohexylphosphide (3) are dissolved in 50 ml of [lacuna] and cooled to −78° C. 2.50 g of a 9:1 mixture of toluene and 1,2,3,4-tetramethylfulvene (1) are subsequently added dropwise. The reaction solution is then warmed to room temperature overnight, resulting in precipitation of the product as a white solid. The monolithium salt (4) is filtered off, washed twice with 10 ml each time of pentane and finally dried under reduced pressure.

Yield: 410 mg (83%)

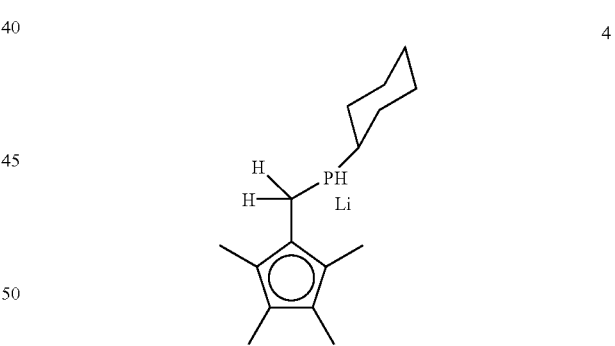

$^1$H-NMR (d$_8$-tetrahydrofuran, 200.1 MHz, 300 K): δ=2.10–0.85 (m, 11H, cyclohexyl-H), 1.84, 1.81 (each s, each 6H, Cp-CH$_3$), 1.72 (d, 2H, $^3J_{HH}$=6.0 Hz, CH$_2$). The PH proton is not observed.

$^{31}$P-NMR (d$_8$-tetrahydrofuran, 81.0 MHz, 300 K): δ=−41.2 (dm, 1J$_{PH}$=192 Hz, PH).

(1-Methyl-1-cyclohexylphosphinoethyl)cyclopentadienyllithium (5)

200 mg (2.20 mmol) of lithium cyclohexylphosphide (3) are dissolved in 50 ml of [lacuna] and cooled to −78° C. 265 mg (2.50 mmol) of 6,6-dimethylfulvene (2) are subsequently added dropwise. The reaction solution is then warmed to room temperature overnight, resulting in precipitation of the product as a white solid. The monolithium salt (5) is filtered off, washed twice with 10 ml each time of pentane and finally dried under reduced pressure.

Note: In a secondary reaction, about 20% of the elimination product (6) is formed.

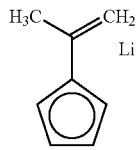

6

Laborious removal of the by-product is omitted at this point, since the compound (6) can be removed more easily during the following steps (second deprotonation, transmetallation to titanium or zirconium). For further information, see below.

The yield of the lithium salt (5) is determined by means of $^1$H-NMR spesctroscopy. See also note.

Yield: 357 mg (71%)

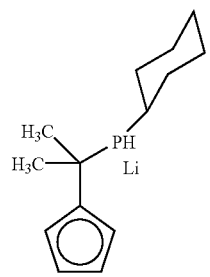

5

$^1$H-NMR (d$_8$-tetrahydrofuran, 200.1 MHz, 300 K): δ=5.62, 5.56 (each m, each 2H Cp-H), 3.00 (d, 1H, $^1$J$_{PH}$=197 Hz, PH), 1.50, 1.44 (each s, each 3H, CH$_3$), 1.73–0.81 (m, 11H, cyclohexyl-H).

$^{31}$P-NMR (d$_6$-benzene/(d$_8$-tetrahydrofuran 4:1, 81.0 MHz, 300 K): δ=6.3 (dm, $^1$J$_{PH}$=197 Hz, PH)

Bis(dialkylamido){η$^5$:κP-1-phosphidomethylcyclopentadienyl} compounds of titanium and zirconium General method of preparing bis(diethylamido)(η$^5$:κP-1-phosphidomethylcyclopentadienyl) compounds of titanium and zirconium A THF solution of the [CpCP] ligand is admixed at 0° C. with the equimolar amount of lithium diisopropylamide, likewise as a solution in THF, stirred for 1 hour and subsequently added to a solution of bis(dimethylamido) dichlorotitanium or bis(diethylamido)dichlorozirconium.bis (tetrahydrofuran) in THF. The reaction solution is stirred for 2 hours, the solvent is removed under reduced pressure and the oily residue is taken up in pentane. The precipitated lithium chloride is filtered off and the filtrate is dried under reduced pressure. The zirconium compounds are isolated as pale reddish brown oils, the titanium compound as a dark red oil.

Bis(dimethylamido)(η$^5$:κP-1-(P-cyclohexylphosphido)-1-methylethylidenecyclopentadienyl)titanium Since the 1-(P-cyclohexyl)phosphino-1-methylethylidenecyclopentadienyllithium used still contained 20% of 1-methylvinylcyclopentadienyllithium according to $^1$H-NMR integration, correspondingly smaller amounts of lithium diisopropylamide (107 mg, 1 mmol) and bis(dimethylamido)dichlorotitanium (195 mg, 0.95 mmol) were reacted with 250 mg of the mixture of the lithium salts. The 1-methylvinylcyclopentadienyllithium did not react and could be separated together with the lithium chloride from the pentane suspension of the product.

Yield: 220 mg (0.62 mmol, 65% based on bis(dimethylamido)dichlorotitanium used

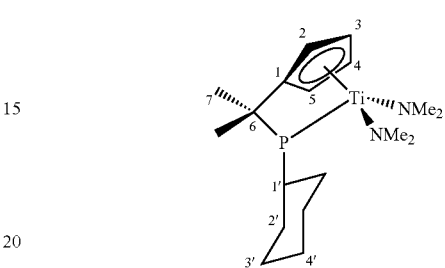

$^1$H-NMR (d$_8$-toluene, 599.8 MHz, 298 K): δ=5.69 (m, 2H, 3-H and 4-H), 5 5.18 (m, 2H, 2-H and 5-H), 2.99 (s, 12H, NCH$_3$), 1.92 (m, 2H, 2'-H), 1.76 (m, 2H, 3'-H), 1.60 (m, 1H, 4'-H), 1.53 (d, $^3$J$_{PH}$=10 Hz, 6H, 7-H), 1.40 (m, 2H, 2'-H), 1.26 (m, 2H, 3'-H), 1.22 (m, 1H, 4'-H), 1.21 (m, 1H, 1'-H).

GCOSY(d$_8$-toluene, 599.8 MHz, 298 K): δ$^1$H/δ$^1$H=5.69/ 5.18 (Cp-H), 1.92/1.76, 1.40 (2'-H/3'-H, 2'-H), 1.76/1.92, 1.60, 1.26 (3'-H/2'-H, 4'-H, 3'-H), 1.60/1.76, 1.22 (4'-H/3'-H, 4'-H), 1.40/1.92, 1.26, 1.21 (2'-H/2'-H, 3'-H, 1'-H).

$^{13}$C-NMR (d$_8$-toluene, 150.8 MHz, 298 K): δ=120.0 (C-1), 110.9 (C-3 and C-4), 107.2 (C-2 and C-5), 46.6 (d, $^3$J$_{PC=5.2}$ Hz, NCH$_3$), 36.7 (d, $^1$J$_{PC=38.3}$ Hz, C-1'), 34.9 (d, $^2$J$_{PC=15.1}$ Hz, C-2'), 30.5 (C-6), 28.8 (d, $^2$J$_{PC=14.6}$ Hz, C-7), 27.7 (d, $^3$J$_{PC=9.3}$ Hz, C-3'), 27.0 (C-4').

GHSQC-NMR (d$_8$-toluene, 150.8/599.8 MHz, 298 K): δ=110.9/5.69 (C-3 and C-4/3-H and 4-H), 107.2/5.18 (C-2 and C-5/2-H and 5-H), 46.6/2.99 (NCH$_3$), 36.7/1.22 (C-1'/ 1'-H), 34.9/1.92, 1.40 (C-2'/2'-H), 28.8/1.53 (C-7/7-H), 27.7/ 1.76, 1.26 (C-3'/3'-H), 27.0/1.60, 1.22 (C-4'/4'-H).

GHMBC-NMR (d$_8$-toluene, 150.8/599.8 MHz, 298 K): δ=120.0, 30.5/1.53 (C-1, C-6/7-H).

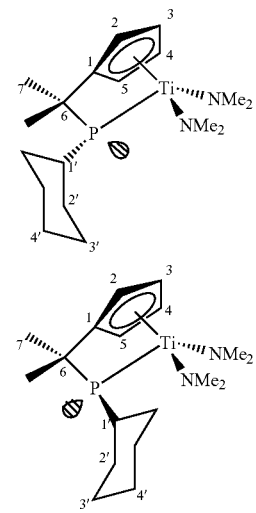

$^1$H-NMR (d$_8$-toluene, 599.8 MHz, 193 K): δ=5.78, 5.61 (b, each 2H, 3-H and 4-H), 5.33, 4.89 (b, each 2H, 2-H and 5-H), 3.06, 2.88 (s, each 12H, NCH$_3$), 2.16 (m, 1H, 1'-H), 2.12 (m, 4H, 2'-H), 1.96 (m, 4H, 3'-H), 1.81 (m, 2H, 4'-H), 1.70 (b, 6H, 7-H), 1.59 (b, 6H, 7-H), 1.46 (m, 4H, 2-H), 1.35 (m, 4H, 3'-H), 1.28 (m, 2H, 4'-H)

$^{13}$C-NMR (d$_8$-toluene, 150.8 MHz, 193 K): δ=120.7 (C-1), 111.2, 110.7 (C-3 and C.4), 108.8, 104.3 (C-2 and C-5), 47.3, 45.0 (b, NCH$_3$), 38.5 (C-1'), 31.9 (C-7), 31.2 (C-2'), 28.3 (C-3'), 26.4 (C-4'), 24.4 (C-7), 22.2 (C-6).

GHSQC-NMR (d$_8$-toluene, 150.8/599.8 MHz, 193 K): δ=111.2/5.61 (C-3 or C-4/3-H or 4-H), 110.7/5.78 (C-3 or C-4/3-H or 4-H), 108.8/4.89 (C-2 or C-5/2-H or 5-H), 104.3/5.33 (C-2 or C-5/2-H or 5-H), 47.3/2.88 (NCH$_3$), 45.0/3.06 (NCH$_3$), 38.9/2.16 (C-1'/1'-H), 31.9/1.70 (C-7/7-H), 31.2/2.12, 1.46 (C-2'/2'-H), 28.3/1.96, 1.35 (C-3'/3'-H), 26.4/1.81, 1.28 (C-4'/4'-H), 24.4/1.59 (C-7/7-H).

GHMBC-NMR (d$_8$-toluene, 150.8/599.8 MHz, 193 K): δ=15 120.7/1.70, 1.59 (C-1, 7-H), 22.2/1.70 (C-6, 7-H).

$^{31}$P-NMR (d$_8$-toluene, 81.0 MHz): δ=14.2 (298 K), 6.3 (273 K), 0.6 (253 K), −5.5 (233 K), −11.4 (213 K), −17.2 (193 K).

Result of dynamic $^1$H-NMR spectroscopy (d$_8$-toluene, 599.8 MHz): Δν of the Cp resonances (T=193 K)=93 Hz (5.78/5.61) or 272 Hz (5.33/4.89). Coalescence temperature T$_c$=213 K or 228 K. ΔG$^≠$=9.8 kcal mol$^{-1}$ or 10.0 kcal mol$^{-1}$

| Elemental analysis: | | | |
|---|---|---|---|
| calculated: | C: 60.67% | H: 9.33% | N: 7.86% |
| found: | C: 61.98% | H: 9.15% | N: 5.53% |

Bis(diethylamido)(η$^5$:κP-1-(P-cyclohexylphosphido)-1-methylethylidenecyclopentadienyl)zirconium Using a method analogous to the synthesis of the titanium compound and taking account of the contamination of the lithium salt, 250 mg of the mixture are reacted with 107 mg of lithium diisopropylamide (1 mmol) and 430 mg of bis(diethylamido)dichlorozirconium.bis(tetrahydrofuran) (0.95 mmol). The product is obtained as a red oil.

Yield: 312 mg (0.67 mmol, 72% based on bis(diethylamido)dichlorozirconium.bis(tetrahydrofuran) used)

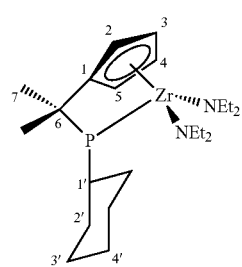

$^1$H-NMR (d$_8$-toluene, 599.8 MHz, 298 K): δ=5.92 (m, 2H, 3-H and 4-H), 5.47 (m, 2H, 2-H and 5-H), 3.26, 3.15 (m, each 4H, NCH$_2$), 1.99 (m, 2H, 2'-H), 1.76 (m, 2H, 3'-H), 1.62 (d, $^3$J$_{PH}$=10 Hz, 6H, 7-H), 1.60 (m, 1H, 1'-H), 1.58 (m, 1H, 4'-H), 1.47 (m, 2H, 2'-H), 1.26 (m, 2H, 3'-H), 1.23 (m, 1H, 4'-H), 0.93 (t, 3J=6.0 Hz, 6H, NCH$_2$CH$_3$).

GCOSY (d$_8$-toluene, 599.8 MHz, 298 K): δ$^1$H/δ$^1$H=5.92/5.47 (Cp-H), $^{13}$C-NMR (d$_8$-toluene, 150.8 MHz, 298 K): 124.0 (C-1), 108.1 (C-3 and C-4), 106.4 (d, $^3$J$_{PC=3.6}$ Hz, C-2 and C-5), 42.5 (d, $^3$J$_{PC<2}$ Hz, NCH$_2$), 36.0 (d, 2J$_{PC=16}$ Hz, C-2'), 35.6 (d, $^1$J$_{PC=38}$ Hz, C-1'), 33.2 (C-6), 30.9 (d, $^2$J$_{PC}$=-13 Hz, C-7), 27.6 (d, $^3$J$_{PC}$=-11 Hz, C-3'), 26.9 (C-4'), 16.1 (NCH$_2$CH$_3$).

GHSQC-NMR (d$_8$-toluene, 150.8/599.8 MHz, 298 K): δ=108.1/5.92 (C-3 and C-4/3-H and 4-H), 106.4/5.47 (C-2 and C-5/2-H and 5-H), 42.5/3.26, 3.15 (NCH$_2$), 36.0/1.99, 1.47 (C-2'/2'-H), 35.6/1.60 (C-1'/1'-H), 30.9/1.62 (C-7/7-H), 27.6/1.76, 1.26 (C-3'/3'-H), 26.9/1.58, 1.23 (C-4'/4'-H), 0.93 (NCH$_2$CH$_3$/NCH$_2$CH$_3$).

GHMBC-NMR (d$_8$-toluene, 150.8/599.8 MHz, 298 K): δ=124.0, 33.5/1.62 (C-1, C-6/7-H).

$^{31}$P-NMR (d$_8$-toluene, 81.0 MHz): δ=−11.5 (298 K), −14.5 (273 K), −16.9 (253 K), −19.1 (233 K), −21.5 (213 K), −24.2 (193 K).

| Elemental analysis: | | | |
|---|---|---|---|
| calculated: | C: 57.98% | H: 9.07% | N: 6.15% |
| found: | C: 58.27% | H: 8.61% | N: 4.91% |

Bis(diethylamido)(η$^5$:κP-1-(P-cyclohexylphosphido)methylidene-2,3,4,5-tetramethylcyclopentadienyl)zirconium 257 mg (1 mmol) of 1-(P-cyclohexyl)phosphinomethyl-2,3,4,5-tetramethylcyclopentadienyllithium are reacted with 107 mg of lithium diisopropylamide (1 mmol) and 430 mg of bis(diethylamido)dichlorozirconium.bis(tetrahydrofuran) (0.95 mmol) to give a reddish brown oil.

Yield: 245 mg (71 mmol, 75% based on bis(diethylamido)dichlorozirconium.bis(tetrahydrofuran) used).

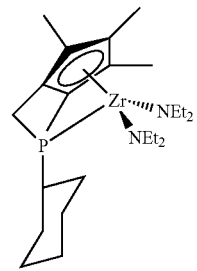

$^1$H-NMR (d$_6$-benzene, 200.13 MHz): δ=3.47–3.22 (m, 8H, NCH$_2$), 2.22–1.02 (m, 11H, C$_6$H$_{11}$), 1.99 (s, 6H, CH$_3$), 1.97 (s, 6H, CH$_3$), 1.06 (t, $^3$J=6.6 Hz, 12H, NCH$_2$CH$_3$).
$^{31}$P-NMR (d$_6$-benzene, 81.0 MHz): δ=−106.4.

Homopolymerization of Norbornene 20 mg of catalyst are added to a solution of 1.75 g of norbornene in 30 ml of a 10% strength MAO solution which had been heated to 80° C. and the mixture is stirred for 20 hours. The reaction mixture is subsequently hydrolyzed with 20 ml of MeOH/1N HCl 1:1, stirred with half-concentrated HCl and the polymer is filtered off, washed and dried.

| Catalyst | Norbornene conversion [%] | Melting point [° C.] |
|---|---|---|
| 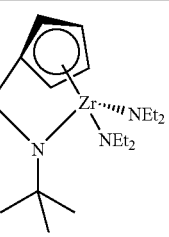 | 70 | 85 |
| 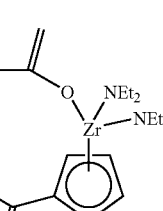 | 100 | 59 |
| 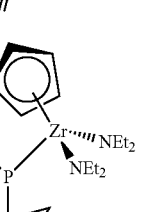 | 100 | 63 |

Polymerization of ethene

| | | | | cat | t | p | T | PE | M.p. | |
|---|---|---|---|---|---|---|---|---|---|---|
| R1 | R2 | R3 | M | [mg] | [h] | [bar] | [° C.] | [g] | [° C.] | Act.* |
| H | Me | Me | Ti | 21 | 1 | 2 | 60 | 13.5 | 132 | 114 |
| H | Me | Et | Zr | 21 | 0.25 | 2 | 60 | 21.0 | 128 | 910 |
| Me | H | Et | Zr | 21 | 1 | 2 | 60 | 9.5 | 126* | 109 |
| ** | | | | 20 | 1 | 2 | 60 | 4.9 | 114 | 52 |
| *** | | | | 18.5 | 1 | 2 | 60 | 0.4 | 128 | 5 |

*[g(PE)/mmol cat*h*bar]
**[(Me₄Cp)-SiMe₂-NtBu]Zr(NMe₂)₂
***[(Me₄Cp)-SiMe₂-NtBu]ZrCl₂///

Note:
200 ml of toluene and 20 ml of MAO are saturated with ethene at an ethene pressure of 2 bar for 1 hour at the reaction temperature indicated.

Copolymerization of ethylene/1-octene

| R1 | R2 | R4 | M | Cat [mg] | M.p. [° C.] | T [h] | P [bar] | T [° C.] | Copo [g] | Ethene:octene | Act.* |
|---|---|---|---|---|---|---|---|---|---|---|---|
| H | Me | Me | Ti | 16 | oil | ½ | 1 | 90 | 0.5 | 5:1 | 22 |
| H | Me | Et | Zr | 21 | solid oil | ½ | 1 | 90 | 51.5 | 6:1 | 2237 |
| Me | H | Et | Zr | 23 | solid oil | ½ | 1 | 90 | 5.8 | 7.5:1 | 244 |
| H | Me | Et | Zr | 22 | solid oil | 1 | 1 | 90 | 67.7 | 6:1 | 1470 |
| Me | H | Et | Zr | 20 | solid oil | 1 | 1 | 90 | 7.1 | 7:1 | 172 |
| ** | | | | 20 | oil | ½ | 1 | 90 | 10.3 | 3:1 | 420 |
| *** | | | | 21 | oil | 1 | 1 | 90 | 4.4 | 3:1 | 83 |

*[g(PE)/mmol cat*h)bar]
**[(Me₄Cp)-SiMe₂-NtBu]Zr(NMe₂)₂
***[(Me₄Cp)-SiMe₂-NtBu]zrCl₂///

Note: 20 ml of MAO and 60 ml of toluene/20 ml of octene or 30 ml of toluene/50 ml of octene are saturated with ethene at the ethene pressure indicated for 1 hour at the reaction temperature indicated. % octene solution = 50

General Method of Preparing Aminoalkylcyclopentadienyllithium Compounds by Addition of a Lithium Amide onto a Fulvene The appropriate amine is added to a solution containing the equimolar amount of lithium diisopropylamide in THF and the mixture is stirred for two hours. The amide generated in situ is then admixed with the equimolar amount of a fulvene. The reaction solution is stirred overnight and subsequently freed of the solvent under reduced pressure. The oily residue is taken up a number of times in pentane and dried again under reduced pressure, but in the case of the N-alkyl derivatives, the product retains its oily consistency.

(1-N-p-Tolylamino-2,2-dimethyl)propylcyclopentadienyllithium 800 mg of LDA (7.46 mmol) and 800 mg (7.46 mmol) of 4-methylaniline are used to generate lithium 4-methylanilide in situ and this is reacted with 1 g (7.46 mmol) of tert-butylfulvene by the above-described work-up to give 2.12 g (7.00 mmol, 89%) of product. The light-brown powder contains 1 equivalent of THF.

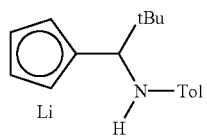

1H-NMR ($d_8$-THF, 200.13 MHz) δ=6.90 (d, 2H, Tol-H), 6.56 (b, 2H, Tol-H), 5.68 (b, 4H, Cp-H), 4.09 (b, 1H, CH), 2.23 (s, 3H, Tol-CH$_3$), 1.02 (s, 9H, C(CH$_3$)$_3$)

(1-N-tert-Butylamino-2,2-dimethyl)propylcyclopentadienyllithium

Lithium tert-butylamide is generated in situ by reaction of 545 mg (7.46 mmol) of tert-butylamine with 800 mg (7.46 mmol) of LDA and subsequently admixed with 1 g (7.46 mmol) of tert-butylfulvene. The product is isolated as a brown oil in a yield of 91% (1.44 g, 6.79 mmol).

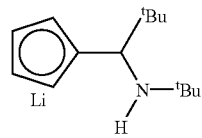

1H-NMR ($d_8$-THF, 200.13 MHz) δ=5.56 (m, 2H, Cp-H), 5.52 (m, 2H, Cp-H, 3.18 (d, 3J=7.0 Hz, 1H, CH), 0.95 (s, 9H, C(CH$_3$)$_3$, 0.83 (s, 9H, C(CH$_3$)$_3$).

13C-NMR ($d_8$-THF, 50.3 MHz): δ=125.4 (ipso-Cp), 103.1 (Cp), 101.1 (Cp), 63.1 (C-1), 30.5 ((CH$_3$)$_3$), 27.9 (C(CH$_3$)$_3$.

1-tert-Butylaminomethyl-2,3,4,5-tetramethylcyclopentadienyllithium 200 mg (2.53 mmol) of lithium tert-butylamide are dissolved in 50 ml of pentane and 2 ml of THF and admixed with 2.5 g of a 9:1 mixture of toluene and 2,3,4,5-tetramethylfulvene. The reaction solution is stirred overnight, which results in precipitation of the product. The solvent is removed under reduced pressure, the residue is taken up in pure pentane and collected on a frit. After washing twice with 20 ml each time of pentane, the white, pulverulent product is dried under reduced pressure.

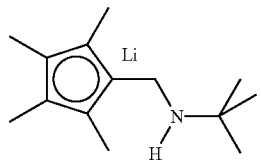

1H-NMR ($d_8$-THF, 200.13 MHz) δ=4.37 (d, 3J=7.0 Hz, 2H, CH), 1.86 (s, 6H, Cp-CH$_3$), 1.82(s, 6H, Cp-CH$_3$), 1.19 (s, 9H, C(CH$_3$)$_3$).

13C-NMR ($d_8$-THF, 50.3 MHz) δ=111.0 (ipso-Cp), 107.3 (Cp), 107.2 (Cp), 50.6 (C(CH$_3$)$_3$), 38.5 (CH$_2$), 29.7 (C(CH$_3$)$_3$), 10.8 (Cp-CH$_3$), 10.6 (Cp-CH$_3$).

6-(N-Arylamido)fulvenyllithium compounds

General method of preparing 6-(N-arylamido)fulvenyllithium compounds

A solution of 6-(dimethylamino)fulvene or of 6-(dimethylamino)-1,2,3,4-tetramethylfulvene in tetrahydrofuran is admixed with the equimolar amount of the lithium anilide, likewise dissolved in tetrahydrofuran, at room temperature and the mixture is subsequently stirred. The reaction time is 2–48 hours, depending on the substituents on the cyclopentadienyl ring and on the phenyl ring. After the reaction is complete, the solvent and the dimethylamine formed are removed under reduced pressure, the resulting viscous oil is firstly covered a number of times with pentane and subsequently freed of the solvent again under reduced pressure. The suspension is then filtered and the residue is dried under reduced pressure. The lithium salts are obtained in high yields (>80%) as light-brown powder.

6-(N-Phenylamido)fulvenyllithium.tetrahydrofuran adduct

The reaction of 3 g (25 mmol) of 6-dimethylamino) fulvene with 2.45 g (25 mmol) of lithium anilide gives, after a reaction time of 2 hours and subsequent work-up, 5.55 g (22.4 mmol) (91%) of 6-N-phenylamidofulvenyllithium.THF adduct. Acicular colorless crystals which are suitable for X-ray structure analysis could be grown from a concentrated THF solution at −20° C.

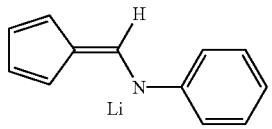

1H-NMR ($d_6$-benzene, 200.13 MHz) δ=8.19 (s, 1H, 6-H), 7.16 (t, m-Ph-H, 2H), 7.00 (d, o-Ph-H, 2H), 6.95 (t, p-Ph-H, 1H), 3.43 (m, α-H-thf, 4H), 1.19 (m, β-H-thf, 2H).

13C-NMR ($d_6$-benzene, 50.3 MHz) δ=158.5 (C-6), 55.5 (ipso-Ph), 129.1, 121.9, 121.2 (all Ph), 120.7 (ipso-Cp), 114.4, 112.8 (both Cp).

7Li-NMR ($d_8$-THF, 70 MHz): δ=−0.89.

N-Phenylamido-2,3,4,5-tetramethylfulvenyllithium

The reaction of 2 g (11 mmol) of 6-dimethylamino-2,3, 4,5-tetramethylfulvene with 1.12 g (11 mmol) of lithium anilide gives, after a reaction time of 24 hours and subsequent work-up, 2.16 g (9.4 mmol) (85%) of N-phenylamido-2,3,4,5-tetramethylfulvenyllithium.

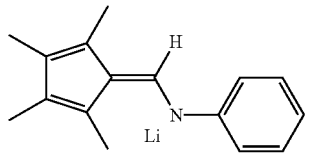

1H-NMR (d$_8$-THF, 200.13 MHz) δ=8.13 (s, 1H), 7.11 (t, m-Ph-H, 2H); 6.89 (d, o-Ph-H, 2H); 6.71 (t, p-Ph-H, 1H); 2.26 (s, 6H); 1.99 (s, 6H).

6-[N-2,6-Diisopropylphenyl)amido]fulvenyllithium.tetrahydrofuran adduct 3 g (25 mmol) of 6-(dimethylamino)fulvene are reacted with 4.52 g (25 mmol) of lithium 2,6-(diisopropyl)anilide. Work-up after a reaction time of 48 hours gives 6.62 g (20 mmol) (81%) of 6-N-(2',6'-diisopropylphenyl)amidofulvenyllithium.THF adduct. Yellow single crystals suitable for X-ray structure analysis could be obtained by cooling a concentrated tetrahydrofuran solution to −20° C.

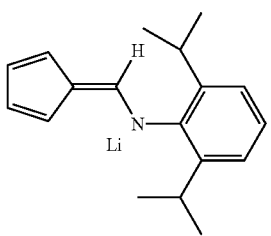

1H-NMR (d$_6$-benzene, 200.13 MHz) δ=8.07, (s, 1H, 1-H), 7.20–7.05 (m, Ph-H, 3H), 6.66 (m, Cp-H, 2H), 6.44 (m, Cp-H, 2H), 3.53 (m, α-H-thf, 4H), 3.42 (sept., 3J=7.0 Hz, 2H, CH(CH$_3$)$_2$)), 1.44 (m, β-H-thf, 4H), 1.19 (d, 3J=7.0 Hz, 12H, CH(CH$_3$)$_2$)).

13C-NMR (d$_6$-benzene, 50.3 MHz) δ=165.5 (C-6), 140.9 (ipso-Ph), 125.3 (p-Ph), 124.8 (o-Ph), 123.9 (ipso-Cp), 123.6 (m-Ph) 112.2 (Cp); 43.0 (CH(CH$_2$)$_2$), 25.4 (CH(CH$_3$)$_2$.

Amidomethylcyclopentadienyldilithium compounds a) by addition onto an amidofulvenyllithium 1-(N-Phenylamido)ethylcyclopentadienyldilithium 3 g (12.1 mmol) of 6-(N-phenylamido)fulvenyllithium.tetrahydrofuran adduct are suspended in 50 ml of diethyl ether, and 7.4 ml of a 1.63 M methyllithium solution in diethyl ether are added dropwise. The reaction solution is stirred for 12 hours and subsequently freed of the solvent. The product is isolated as a brown powder and still contains 0.75 equivalents of THF. The yield is 2.93 g (11.6 mmol, 96%).

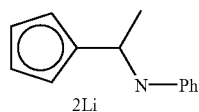

1H-NMR (d$_8$-THF, 200.1 MHz) δ=6.69 (t, 3J$_{H-H}$=7.2 Hz, 2H, M-Ph-H), 6.29 (d, 3J$_{H-H}$=7.2 Hz, 2H, o-Ph-H), 5.80 (t, 3J$_{H-H}$=7.1 Hz, 1H, p-Ph-H), 5.66 (b, 4H, Cp-H), 4.25 (q, 3J$_{H-H}$=6.0 Hz, 1H, H-1), 1.26 (d, 3J$_{H-H}$=6.0 Hz, 3H, H-2) ppm.

[(N-Phenylamido)-p-toyl]methylcyclopentadienyldilithium 988 mg (4 mmol) of 6-(N-phenylamido)fulvenyllithium.tetrahydrofuran adduct, dissolved in 50 ml of THF, are admixed with a solution of 392 mg (4 mmol) of p-tolyllithium in 30 ml of THF. The brown solution is stirred overnight, and the solvent is subsequently removed under reduced pressure. The residue is taken up twice in pentane and brought to dryness again, so that 1.03 g (3.76 mmol, 94%) of the brown, pulverulent product are finally able to be isolated.

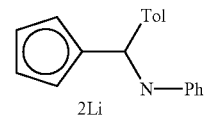

1H-NMR (d$_8$-THF, 200.1 MHz) δ=7.25 (d, 3J$_{H-H}$=7.4 Hz, 2H, Tol-H), 6.88 (d, 3J$_{H-H}$=7.4 Hz, 2H, Tol-H); 5.80 (t, 3J$_{H-H}$=8.0 Hz, 2H, m-Ph-H); 6.20–5.80 (b, 3H, o- and p-Ph-H), 5.67 (m, 2H, Cp-H); 5.53 (b, 2H, Cp-H), 5.12 (s, 1H, H-1); 2.22 (s, 3H, Tol-CH$_3$).

b) by deprotonation of an aminomethylcyclopentadienyllithium salt (1-N-p-Tolylamido-2,2-dimethyl)propylcyclopentadienyllithium 2.12 g (7.00 mmol) of (1-N-p-tolylamino-2,2-dimethyl)propylcyclopentadienyllithium.THF are dissolved in 50 ml of THF and admixed with 756 mg (7.00 mmol) of LDA, likewise dissolved in 30 ml of THF, at 0° C. After a reaction time of 3 hours, the solvent is removed under reduced pressure and the product is converted into a powder by covering it a number of times with pentane and subsequently drying it under reduced pressure each time The yield is 1.34 g (87%, 6.1 mmol).

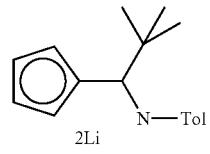

1H-NMR (d$_8$-THF, 200.1 MHz) δ=6.38 (d, 3J$_{H-H}$=8.0 Hz, 2H, Tol-H), 6.05 (b, 2H, Tol-H), 5.63 (b, 4H, Cp-H), 4.05 (s, 1H, H-1), 2.01 (s, 3H, Tol-CH$_3$), 0.98 (s, 9H, C(CH$_3$)$_3$).

(1-N-tert-Butylamido-2,2-dimethyl)propylcyclopentadienyldilithium 1.2 g (5.64 mmol) of (1-N-tert-butylamino-2,2-dimethyl)propylcyclopentadienyllithium are dissolved in 30 ml of THF and admixed at −78° C. with 3.7 ml of a 1.52 M tert-butyllithium solution in hexane. The reaction solution is stirred overnight and then freed of the solvent. The oily residue is stirred in pentane and the light-yellow powder which precipitates is collected on a frit and dried under reduced pressure. The product is obtained in a virtually quantitative yield of 98% (1.21 g, 5.53 mmol)

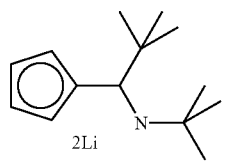

1H-NMR (d$_8$-THF, 200.13 MHz ) δ=5.7–5.5 (b, 4H, Cp-H), 3.29 (s, 1H, 1-H), 1.13 (s, 9H, C(CH$_3$)$_3$), 0.95 (s, 9H, C(CH$_3$)$_3$)

1-tert-Butylaminomethyl-2,3,4,5-tetramethylcyclopentadienyldilithium 200 mg (0.98 mmol) of tert-butylaminomethyl-2,3,4,5-tetramethylcyclopentadienyllithium are dissolved in 50 ml of THF, and 0.63 ml of a 1.56 M tert-butyllithium solution in hexane is added slowly at −78° C. The reaction solution is stirred overnight, the precipitate is filtered off, washed with 10 ml of pentane and dried under reduced pressure. This gives 188 mg (0.88 mmol, 90%) of the product as a white powder which is soluble in none of the solvents used and could thus not be characterized by NMR spectroscopy.

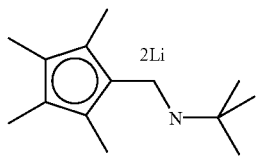

bis(Diethylamido)(η$_5$:κN-1-amidomethylcyclopentadienyl) compounds of titanium and zirconium General method for preparing the bis-(diethylamido)(η$^5$:κN-1-amidomethylcyclopentadienyl) compounds of titanium and zirconium A THF solution of the dianionic [Cp,N] ligand is added at 0° C. to a solution of bis(dimethylamido)dichlorotitanium or bis(diethylamido)dichlorozirconium.bis-(tetrahydrofuran) adduct in THF. The reaction solution is stirred for 2 hours, the solvent is removed under reduced pressure and the oily residue is taken up in pentane. The lithium chloride which precipitates is filtered off and the filtrate is dried under reduced pressure. The product is obtained as a yellow-brown oil in the case of all the zirconium compounds; only the titanium compound is isolated as a dark red powder.

bis(Dimethylamido){η$^5$:κN-1-(N-phenylamido)-tert-butylmethylcyclopentadienyl}titanium 231 mg (1.12 mmol) of bis(dimethylamido)dichlorotitanium and 370 mg (1.12 mmol) of (1-N-p-tolylamido-2,2-dimethyl)propylcyclopentadienyldilithium give 276 mg (0.80 mmol, 71%) of product in the form of a dark red powder.

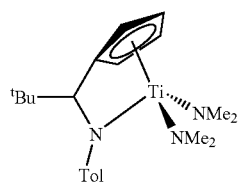

1H-NMR (d$_6$-benzene, 599.8 MHz ) δ=7.02 (d, 3J=6.6 Hz, 2H, m-Tol-H), 6.99 (t, 3J=6.6 Hz, 2H, o-Tol-H), 6.16, 5.73 (m, each 1H, 1'-H), 6.12, 5.83 (m, each 1H, 2'-H), 4.85 (s, 1H, 1-H), 3.02, 2.87 (s, each 6H, NHC$_3$), 2.19 (s, 3H, Tol-CH$_3$), 1.14 (s, 9H, 3-H).

GCOSY (d$_6$-benzene, 599.8 MHz): δ$^1$H/δ$^1$H=7.02/6.99 (m-/o-Tol-H), 6.99/7.02 (o-/m-Tol-H), 6.16/6.12, 5.83, 5.73 (Cp-H).

13C-NMR (d$_6$-benzene, 150.8 MHz): 154.0 (ipso-Tol), 129.1 (m-Tol), 128.5 (p-Tol), 119.2 (o-Tol), 116.7 (C-1'), 114.8 (C-1'), 114.8 (ipso-Cp), 114.7 (C-2'), 111.3 (C-2'), 68.1 (C-1), 48.9, 47.0 (both NCH$_3$), 38.0 (C-2), 28.6 (C-3), 20.8 (Tol-CH$_3$).

GHSQC-NMR (d$_6$-benzene, 150.8/599.8 MHz ): δ=129.1/7.02 (m-Tol-C)/m-Tol-H), 119.2/6.99 (o-Tol-C)/o-Tol-H), 116.7/5.73 (C-1'/1'-H), 114.8/6.16 (C-1'/1'-H), 114.7/6.12 (C-2'/2'-H), 111.3/5.83 (C-2'/2'-H), 68.1/4.85 (C-1/1-H), 48.9/2.87 (NCH$_3$), 47.0/3.02 (NCH$_3$), 28.8/1.14 (C-3/3-H), 20.8/2.19 (Tol-CH$_3$/Tol-CH$_3$)

bis(Diethylamido)(η$^5$:κN-1-(N-phenylamido)ethylcyclopentadienyl)zirconium

The reaction of 2.5 g (5.6 mmol) of bis(diethylamido)dichlorozirconiumbis(tetrahydrofuran) adduct and 1.5 g (5.6 mmol) of 1-(N-phenylamido)ethylcyclopentadienyldilithium gives 1.6 g (3.84 mmol, 69%) of the reddish-brown, oily product.

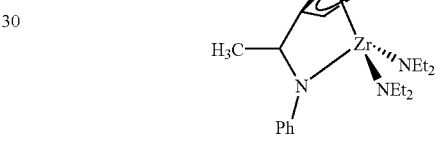

1H-NMR (d$_6$-benzene, 599.8 MHz ): δ=7.26 (d, 3J=7.8 Hz, 2H, m-Ph-H), 6.87 (t, 3J=7.2 Hz, 2H, o-Ph-H), 6.74 (t, 3J=7.2 Hz, 1H, p-Ph-H), 6.31, 6.00 (m, each 1H, Cp-H), 6.07 (m, 2H, Cp-H), 5 00 (q, 3J=6.6Hz, 1H, 1-H), 3.33, 3.24, 3.19, 3.07 (m, each 2H, NCH$_2$), 1.52 (d, 3J=6.6 Hz, 3H, 2-H), 1.00 (t, 3J=6.6 Hz, 6H, NCH$_2$CH$_3$), 0.77 (t, 3J=6.6 Hz, 6H, NCH$_2$CH$_3$).

TOCSY (d$_6$-benzene, 599.8 MHz): irradiation at δ=1.52, secondary signal at 5.00, irradiation at δ=1.00, secondary signals at 3.24, 3.19, irradiation at δ=0.77, secondary signals at 3.33, 3.07.

13C-NMR (d$_6$-benzene, 150.8 MHz ): δ=152.0 (ipso-Ph) 129.2 (m-Ph), 117.1 (p-Ph), 115.1 (o-Ph), 114.3, 111.6, 111.2, 109.6 (all Cp), 51.4 (C-1), 43.8, 43.0 (both NCH$_2$), 17.8 (C-2), 16.1, 15.9 (both NCH$_2$CH$_3$)

GHSQC-NMR (d$_6$-benzene, 150.8/599.8 MHz): δ=129.2/7.26 (m-Ph-H)/m-Ph-C), 117.1/6.74 (p-Ph-C/p-Ph-H), 115.1/6.87 (o-Ph-C/o-Ph-H), 114.3/6.00 (Cp-C/Cp-H0, 111.6/6.31 (Cp-C/Cp-H), 111.2/6.07 (Cp-C/Cp-H), 109.6/6.07 (Cp-C/Cp-H), 51.4/5.00 (C-1/1-H), 43.8/3.24, 3.19 (NCH$_2$/NCH$_2$), 43.0/3.33, 3.07 (NCH$_2$/NCH$_2$), 17.8/1.52 (C-2/2-H), 16.1/1.00 (NCH$_2$CH$_3$/NCH$_2$CH$_3$), 15.9/0.77 (NCH$_2$CH$_3$/NCH$_2$CH$_3$).

| Elemental analysis: | | | |
| --- | --- | --- | --- |
| calculated: | C: 60.23% | H: 7.94% | N: 10.08% |
| found: | C: 59.28% | H: 8.32% | N: 9.41% | bis(Diethylamido){η⁵:κN-1-(N-phenylamido)-p-tolylmethylcyclopentadienyl}zirconium 900 mg (2 mmol) of bis(diethylamido)dichlorozirconium.bis-(tetrahydrofuran) adduct and 548 mg of [(N-phenylamido)-p-tolyl]methylcyclopentadienyldilithium are reacted to form 741 mg (1.5 mmol, 75%) of the dark brown, oily product.

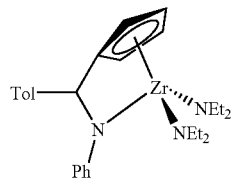

1H-NMR (d₆-benzene, 599.8 MHz ): δ=7.37 (d, 3J=7.8 Hz, 2H, o-Tol-H), 7.18 (t, 3J=7.2 Hz, 2H, m-Ph-H), 7.02 (d, 3J=7.8 Hz, 2H, m-Tol-H), 6.91 (d, 3J=7.8 Hz, 2H, o-Ph-H), 6.70 (t, 3J=7.8 Hz, 1H, p-Ph-H), 6.14, 5.90 (m, each 1H, 1'-H), 6.00, 5.96 (m, each 1H, 2'-H), 6.03 (s, 1H, 1-H), 3.38, 3.37, 3.28, 3.16 (m, each 2H, NCH₂), 2.12 (s, 3H, Tol-CH₃), 1.01 (t, 3J=6.6 Hz, 6H, NCH₂CH₃), 0.87 (t, 3J=6.6 Hz, 6H, NCH₂CH₃).

GCOSY (d₆-benzene, 599.8 MHz ): δ¹H/δ¹H=7.37/7.02 (m-/o-Tol-H), 7.18/6.91, 6.70 (m-/o-, p-Ph-H), 7.02/7.37 (o-/m-Tol-H), 6.91/7.18 (o-/m-Ph-H), 6.70/7.18 (p-/m-Ph-H), 6.14/6.10, 5.96, 5.90 (Cp-H), 3.38, 3.16/0.87 (NCH₂/NCH₂CH₃), 3.37, 3.28/1.01 (NCH₂/NCH₂CH₃). TOCSY (d₆-benzene, 599.8 MHz ): irradiation at δ=7.37, secondary signal at 7.02, irradiation at δ=6.70, secondary signals at 7.18, 6.91, irradiation at δ=1.01, secondary signals at 3.37, 3.28, irradiation at δ=0.87, secondary signals at 3.37, 3.16.

13C-NMR (d₆-benzene, 150.8 MHz ): 152.2 (ipso-Ph), 139.7 (p-Tol), 136.2 (ipso-Tol), 129.4 (m-Tol), 129.1 (m-Ph), 127.0 (o-Tol), 117.2 (p-Ph), 115.4 (o-Ph), 114.4 (ipso-Cp), 114.3, 114.0 (both C-1'), 111.0, 110.5 (both C-2'), 60.2 (C-1), 43.7, 43.1 (both NCH₂), 21.1 (Tol-CH₃), 16.0 (NCH₂CH₃).

GHSQC-NMR (d₆-benzene, 150.8/599.8 MHz ): δ=129.4/7.02 (o-Tol-C/o-Tol-H), 129.1/7.18 (m-Ph-C/m-Ph-H), 127.0/7.38 (m-Tol-C/m-Tol-H), 117.2/6.70 (p-Ph-C/p-Ph-H), 115.4/6.91 (o-Ph-C/o-Ph-H), 114.3/6.14 (C-1'/1'-H), 114.0/5.90 (C-1'/1'-H), 111.0/6.00 (C-2'/2'-H), 110.5/5.96 (C-2'/2'-H), 60.2/6.03 (C-1/1-H), 43.7/3.37, 3.28 (NCH₂/NCH₂), 43.1/3.38, 3.16 (NCH₂/NCH₂), 21.1/2.12 (Tol-CH₃/Tol-CH₃), 16.0/1.01, 0.87 (NCH₂/CH₃/NCH₂/CH₃)

| Elemental analysis: | | | |
|---|---|---|---|
| calculated: | C: 65.54% | H: 7.53% | N: 8.49% |
| found: | C: 65.85% | H: 7.97% | N: 8.52% | bis(Diethylamido){η⁵:κN-1-(N-phenylamido)-tert-butylmethylcyclopentadienyl}zirconium Reaction of 450 mg (1 mmol) of bis(diethylamido)dichlorozirconium.bis(tetrahydrofuran) adduct with 325 mg (1 mmol) of (1-N-p-tolylamido-2,2-dimethyl)propylcyclopentadienyldilithium gives 313 mg (0.66 mmol, 66%) of the orange-brown, oily product.

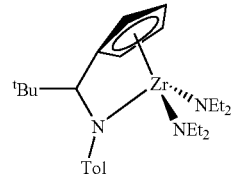

1H-NMR (d₆-benzene, 599.8 MHz ): 6.98 (d, 3J=6.6 Hz, 2H, m-Tol-H), 6.94 (t, 3J=6.6 Hz, 2H, o-Tol-H), 6.38, 5.93 (m, each 1H, 1'-H), 6.10, 6.07 (m, each 1H, 2'-OH), 4.96 (s, 1H, 1-H), 3.31, 3.28, 3.19, 3.08 (m, each 2H, NCH₂), 2.19 (s, 3H, Tol-CH₃), 1.19 (s, 9H, 3-H), 1.06 (t, 3J=4.8 Hz, 6H, NCH₂CH₃), 0.65 (t, 3J=4.8 Hz, 6H, NCH₂CH₃).

GCOSY (d₆-benzene, 599.8 MHz): δ¹H/δ¹H=6.98/6.94 (m-/o-Tol-H), 6.94/6.98 (o-/m-Tol-H), 6.38/6.10, 6.07, 5.93 (Cp-H), 3.31, 3.28/1.06 (NCH₂/NCH₂CH₃), 3.19, 3.08/0.65 (NCH₂/NCH₂CH₃).

13C-NMR (d₆-benzene, 150.8 MHz): 152.3 (ipso-Tol), 129.7 (m-Tol), 127.4 (p-Tol), 119.0 (o-Tol), 115.5 (C-1'), 113.0 (C-1), 112.8 (ipso-Cp), 111.6 (C-2'), 109.7 (C-2'), 66.2 (C-1), 43.6, 43.2 (both NCH₂), 38.7 (C-2), 28.8 (C-3), 20.8 (Tol-CH₃), 15.7, 15.3 (both NCH₂CH₃).

GHSQC-NMR (d₆-benzene, 150.8/599.8 MHz): δ=129.7/6.98 (m-Tol-C/m-Tol-H), 119.0/6.94 (o-Tol-C/o-Tol-H), 115.5/5.93 (C-1'/1'-H), 113.0/6.38 (C-1'/1'-H), 111.6/6.10 (C-2'/2'-H), 109.7/6.07 (C-2'/2'-H), 66.2/4.96 (C-1/1-H), 43.6/3.31, 3.28 (NCH₂/NCH₂), 43.2/3.19, 3.08 (NCH₂/NCH₂), 28.8/1.19 (C-3/3-H), 20.8/2.19 (Tol-CH₃/Tol-CH₃), 15.7/1.06 (NCH₂CH₃/NCH₂/CH₃), 15.3/0.65 (NCH₂CH₃/NCH₂CH₃).

| Elemental analysis: | | | |
|---|---|---|---|
| calculated: | C: 63.23% | H: 8.70% | N: 8.85% |
| found: | C: 63.03% | H: 8.01% | N: 8.34% | bis(Diethylamido){η⁵:κN-1-(N-tert-butylamido)-tert-butylmethylcyclopentadienyl}zirconium 450 mg (1 mmol) of bis(diethylamido)dichlorozirconium-bis(tetrahydrofuran) adduct and 219 mg (1 mmol) of (1-N-tert-butylamido-2,2-dimethyl)propylcyclopentadienyldilithium give 313 mg (0.71 mmol, 71%) of the light-green, oily product.

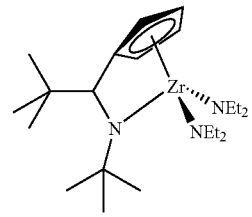

1H-NMR (d₂-dichloromethane, 599.8 MHz): 6.30, 5.73 (m, each 1H, 1'-H), 6.13, 5.99 (m, each 1H, 2'-H), 4.40 (s, 1H, 1-H), 3.40, 3.19, 3.14, 3.07 (m, each 2H, NCH₂), 1.30 (s, 9H, NC(CH₃)₃), 1.19 (s, 9H, CC(CH₃)₃), 0.96 (t, 3J=4.8 Hz, 6H, NCH₂CH₃), 0.92 (t, 3J=4.8 Hz, 6H, NCH₂CH₃).

GCOSY (d$_2$-dichloromethane, 599.8 MHz ): δ$^1$H/δ$^1$H=3.40, 3.07/0.92 (NCH$_2$/NCH$_2$CH$_3$), 3.19, 3.14/0.96 (NCH$_2$/NCH$_2$CH$_3$).

13C-NMR (d$_2$-dichloromethane, 150.8 MHz): 113.8 (C-1'), 112.6 (C-1'), 110.6 (C-2'), 107.6 (C-2'), 68.6 (C-1), 55.2 (NC(CH$_3$)$_3$), 45.2, 42.1 (both NCH$_2$), 35.6 (CC(CH$_3$)$_3$), 31.1 (NC(CH$_3$)$_3$, 29.7 (CC(CH$_3$)$_3$), 15.4, 13.9 (both NCH$_3$CH$_3$).

GHSQC-NMR (d$_2$-dichloromethane, 150.8/599.8 MHz): δ=113.8/5.73 (C-1'/1'-H), 112.6/6.30 (C-1'/1'-H), 110.6/6.13 (C-2'/2'-H), 107.6/5.99 (C-2'/2'-H), 68.6/4.40 (C-1/1-H), 45.2/3.40, 3.07 (NCH$_2$/NCH$_2$), 42.1/3.19, 3.14 (NCH$_2$/NCH$_2$), 31.1/1.30 (NC/CH$_3$)$_3$/NC(CH$_3$)$_3$, 29.7/1.19 (CC(CH$_3$/CC(CH$_3$)$_3$), 15.4/0.92 (NCH$_2$CH$_3$/NCH$_2$CH$_3$), 13.9/0.96 (NCH$_2$CH$_3$/NCH$_2$CH$_3$).

bis(Diethylamido){η$^5$:κN-(N-tert-butylamidomethyl-2,3,4,5-tetramethylcyclopentadienyl}zirconium The compound could be obtained cleanly in an NMR experiment. For this purpose, 21 mg (0.1 mmol) of 1-tert-butylaminomethyl-2,3,4,5-tetramethylcyclopentadienyldilithium and 45 mg (0.1 mmol) of bis(diethyl-amido)dichlorozirconium.bis(tetrahydrofuran) adduct were weighed into an NMR tube and reacted in 0.5 ml of d$_8$-THF. The suspension becomes clear after about 30 minutes when the dilithium salt has reacted completely. It was not possible to synthesize and isolate the compound on a preparative scale.

What is claimed is:

1. A process for preparing compounds of the formula (VII)

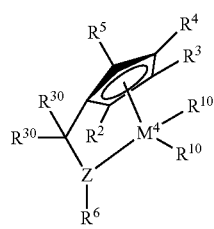

(VII)

where

R$^{30}$ is a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl, or fluorinated C$_7$–C$_{20}$-alkylaryl, R$^8$ is a hydrogen atom or C$_1$–C$_{18}$-alkyl, R$^2$, R$^3$, R$^4$, R$^5$ are identical or different and are each a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, where R$^2$, R$^3$, R$^4$, R$^5$ may together from cyclic systems which may in turn by substituted, R$^6$ is a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl or C$_7$–C$_{20}$-alkylaryl, R$^{10}$ is a hydrogen atom, a halogen atom, C$_1$–C$_{18}$-alkyl, C$_3$–C$_{12}$-cycloalkyl, C$_6$–C$_{20}$-aryl, C$_6$–C$_{20}$-aryloxy, C$_1$–C$_{20}$-alkyloxy or a nitrogen-containing compound, Z is phosphorus or nitrogen, M$^4$ is an element of groups 3 to 8 of the Periodic Table of Elements, comprising the steps A) reacting a compound of the formula I

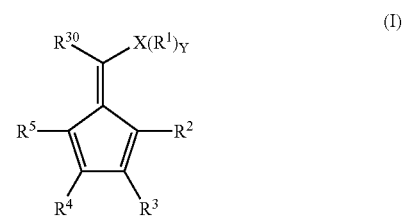

(I)

where

R$^1$ are identical or different and are each a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl, or fluorinated C$_7$–C$_{20}$-alkylaryl, and R$^2$, R$^3$, R$^4$, R$^5$ are as defined under formula (VII), X is nitrogen, Y is 2, R$^{30}$ is as defined above, with a compound of the formula (II)

M$^1$R$^6$ZR$^7$ (II)

where

Z and R$^6$ are as defined under formula (VII),

M$^1$ is an element of group 1 or 2 of the Periodic Table of the Elements,

R$^7$ is a hydrogen atom, to form a compound of the formula (III)

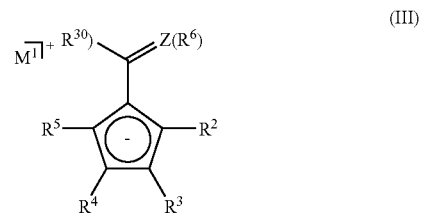

(III)

where R$^2$, R$^3$, R$^4$, R$^5$, R$^6$, R$^{30}$, Z and M$^1$ are as defined above, B) reacting the compound of the formula (III) obtained in step A) with a compound of the formula IV

M$^2$R$^8$ (IV)

where

M$^2$ is an element of group 1 of the Periodic Table of the Elements,

R$^8$ is a hydrogen atom or C$_1$–C$_{18}$-alkyl, to form a compound of the formula (V)

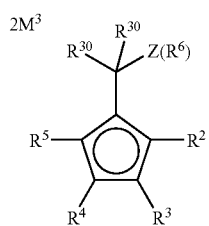

(V)

where
R$^2$, R$^3$, R$^4$, R$^5$, R$^6$, R$^8$, R$^{30}$, and Z are as defined above and
M$^3$ is an element of group 1 of the Periodic Table of the Elements, and
C) reacting the compound of the formula (V) obtained in step B) with a compound of the formula (VI)

(VI)

where
M$^4$ is an element of group 3 to 8 of the Periodic Table of the Elements,
R$^9$ is a hydrogen atom, a halogen atom, a C$_1$–C$_{18}$-alkyl, C$_3$–C$_{12}$-cycloalkyl, C$_6$–C$_{20}$-aryl, C$_6$–C$_{20}$-aryloxy or C$_1$–C$_{20}$-alkyloxy,
R$^{10}$ is a hydrogen atom, a halogen atom, a C$_1$–C$_{18}$-alkyl, C$_3$–C$_{12}$-cycloalkyl, C$_6$–C$_{20}$-aryl, C$_6$–C$_{20}$-aryloxy, C$_1$–C$_{20}$-alkyloxy or a nitrogen-containing compound,
R$^{11}$ is a C$_1$–C$_{20}$-heteroorganic compound,
f is 1–10,
g is 1–10,
k is 1–10,
to give the compound of the formula (VII).

2. A compound of the formula (VII-A)

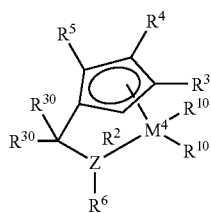

(VII-A)

where
R$^{30}$ is a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl, or fluorinated C$_7$–C$_{20}$-alkylaryl, where the R$^{30}$ substituents do not both have the same meaning,
R$^2$, R$^3$, R$^4$, R$^5$ are identical or different and are each a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, where the radicals R$^2$, R$^3$, R$^4$, and R$^5$ may together from cyclic systems which may in turn be substituted,
R$^6$ is a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylkalkyl or C$_7$–C$_{20}$-alkylaryl,
R$^{10}$ is a hydrogen atom, a halogen atom, a C$_1$–C$_{18}$-alkyl, C$_3$–C$_{12}$-cycloalkyl, C$_6$–C$_{20}$-aryl, C$_6$–C$_{20}$-aryloxy, C$_1$–C$_{20}$-alkyloxy or a nitrogen-containing compound,
Z is phosphorus or nitrogen,
M$^4$ is an element of group 3 to 8 of the Periodic Table of the Elements.

3. A catalyst system comprising
A) at least one cocatalyst,
B) at least one compound of the formula (VII-A) as claimed in claim 2,
C) optionally, at least one support.

4. A process for the polymerization of olefins, said process comprising polymerizing said olefins in the presence of compound (VII-A) of claim 2.

5. A process for the polymerization of olefins, said process comprising polymerizing said olefins in the presence of the catalyst system of claim 3.

6. A compound of the formula (VII-A)

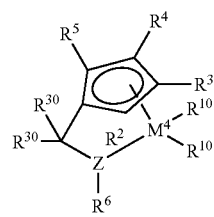

(VII-A)

where
R$^{30}$ is a C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl, or fluorinated C$_7$–C$_{20}$-alkylaryl, where the R$^{30}$ substituents have the same meaning,
R$^2$, R$^3$, R$^4$, R$^5$ are identical or different and are each a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, where the radicals R$^2$, R$^3$, R$^4$, and R$^5$ may together from cyclic systems which may in turn be substituted,
R$^6$ is a hydrogen atom, C$_1$–C$_{18}$-alkyl, C$_3$–C$_{12}$-cycloalkyl, C$_2$–C$_{10}$-alkenyl, C$_3$–C$_{15}$-alkylalkenyl, C$_6$–C$_{18}$-aryl, C$_5$–C$_{18}$-heteroaryl, C$_7$–C$_{20}$-arylkalkyl or C$_7$–C$_{20}$-alkylaryl,
R$^{10}$ is a hydrogen atom, a halogen atom, a C$_1$–C$_{18}$-alkyl, C$_3$–C$_{12}$-cycloalkyl, C$_6$–C$_{20}$-aryl, C$_6$–C$_{20}$-aryloxy, C$_1$–C$_{20}$-alkyloxy or a nitrogen-containing compound,
Z is phosphorus,
M$^4$ is an element of group 3 to 8 of the Periodic Table of the Elements.

7. A catalyst system comprising
A) at least one cocatalyst,
B) at least one compound of the formula (VII-A) as claimed in claim 6,
C) optionally, at least one support.

8. A process for the polymerization of olefins, said process comprising polymerizing said olefins in the presence of the catalyst system of claim 7.

9. A compound of the formula (VII-A)

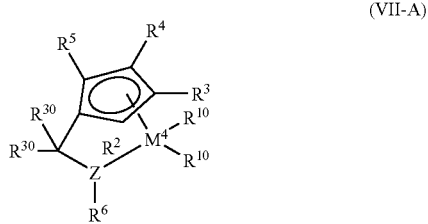

where $R^{30}$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl, or fluorinated $C_7$–$C_{20}$-alkylaryl, where the $R^{30}$ substituents have the same meaning, $R^2$, $R^3$, $R^4$, $R^5$ are identical or different and are each a hydrogen atom, ethyl, n-butyl, n-hexyl, isopropyl, isobutyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where the radicals $R^2$, $R^3$, $R^4$, $R^5$ may together from cyclic systems which may in turn be substituted $R^6$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylkalkyl or $C_7$–$C_{20}$-alkylaryl, $R^{10}$ is a hydrogen atom, a halogen atom, a $C_1$–$C_{18}$-alkyl, $C_3$–$C_{12}$-cycloalkyl, $C_6$–$C_{20}$-aryl, $C_6$–$C_{20}$-aryloxy, $C_1$–$C_{20}$-alkyloxy or a nitrogen-containing compound, Z is phosphorus, $M^4$ is an element of group 3 to 8 of the Periodic Table of the Elements.

10. A catalyst system comprising
A) at least one cocatalyst,
B) at least one compound of the formula (VII-A) as claimed in claim 9,
C) optionally, at least one support.

11. A process for the polymerization of olefins, said process comprising polymerizing said olefins in the presence of the catalyst system of claim 10.

12. A compound of the formula (VII-A)

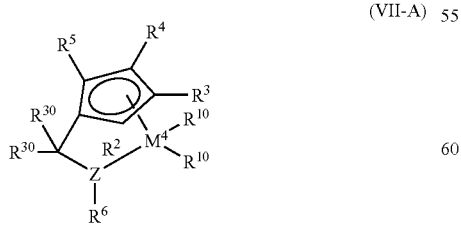

where $R^{30}$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl, or fluorinated $C_7$–$C_{20}$-alkylaryl, where the $R^{30}$ substituents have the same meaning, $R^2$, $R^3$, $R^4$, $R^5$ are identical or different and are each a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where the radicals $R^2$, $R^3$, $R^4$ and $R^5$ may together from cyclic systems which may in turn be substituted, $R^6$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_5$–$C_{18}$-heteroaryl, $C_7$–$C_{20}$-arylkalkyl or $C_7$–$C_{20}$-alkylaryl, $R^{10}$ is a hydrogen atom, a halogen atom, a $C_1$–$C_{18}$-alkyl, $C_3$–$C_{12}$-cycloalkyl, $C_6$–$C_{20}$-aryl, $C_6$–$C_{20}$-aryloxy, $C_1$–$C_{20}$-alkyloxy or a nitrogen-containing compound, Z is phosphorus, $M^4$ is an element of group 3 to 8 of the Periodic Table of the Elements.

13. A catalyst system comprising
A) at least one cocatalyst,
B) at least one compound of the formula (VII-A) as claimed in claim 12,
C) optionally, at least one support.

14. A process for the polymerization of olefins, said process comprising polymerizing said olefins in the presence of the catalyst system of claim 13.

15. A compound of the formula (VII-A)

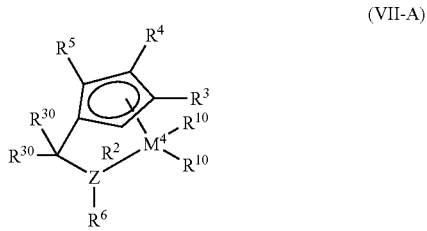

where $R^{30}$ is a hydrogen atom $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl, or fluorinated $C_7$–$C_{20}$-alkylaryl, where the $R^{30}$ substituents have the same meaning, $R^2$, $R^3$, $R^4$, $R^5$ are identical or different and are each a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where the radicals $R^2$, $R^3$, $R^4$, and $R^5$ may together from cyclic systems which may in turn be substituted, $R^6$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylkalkyl or $C_7$–$C_{20}$-alkylaryl, $R^{10}$ is a hydrogen atom, a halogen atom, a $C_1$–$C_{18}$-alkyl, $C_3$–$C_{12}$-cycloalkyl, ($C_6$–$C_{20}$-aryloxy, $C_1$–$C_{20}$-alkyloxy or a nitrogen-containing compound, Z is phosphorus, $M^4$ is an element of group 3 to 8 of the Periodic Table of the Elements.

16. A catalyst system comprising
A) at least one cocatalyst,
B) at least one compound of the formula (VII-A) as claimed in claim 13,
C) optionally, at least one support.

17. A process for the polymerization of olefins, said process comprising polymerizing said olefins in the presence of the catalyst system of claim 16.

18. A compound of the formula (VII-A)

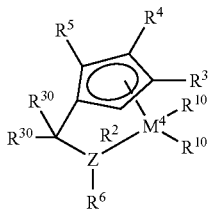

(VII-A)

where $R^{30}$ is a hydrogen atom $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl, or fluorinated $C_7$–$C_{20}$-alkylaryl, where the $R^{30}$ substituents have the same meaning, $R^2$, $R^3$, $R^4$, $R^5$ are identical or different and are each a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where the radicals $R^2$, $R^3$, $R^4$ and $R^5$ may together from cyclic systems which may in turn be substituted, $R^6$ is a hydrogen atom, $C_1$–$C_{18}$-alkyl, $C_3$–$C_{12}$-cycloalkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylkalkyl or $C_7$–$C_{20}$-alkylaryl, $R^{10}$ is a hydrogen atom, a halogen atom, a $C_1$–$C_{18}$-alkyl, $C_3$–$C_{12}$-cycloalkyl, $C_6$–$C_{20}$-aryl, $C_6$–$C_{20}$-aryloxy, $C_1$–$C_{20}$-alkyloxy or a nitrogen-containing compound, Z is phosphorus, $M^4$ is zirconium or hafnium.

19. A catalyst system comprising
A) at least one cocatalyst,
B) at least one compound of the formula (VII-A) as claimed in claim 18,
C) optionally, at least one support.

20. A process for the polymerization of olefins, said process comprising polymerizing said olefins in the presence of the catalyst system of claim 19.

* * * * *